US012269835B2

(12) United States Patent
Zhou et al.

(10) Patent No.: US 12,269,835 B2
(45) Date of Patent: Apr. 8, 2025

(54) PREPARATION METHOD FOR AND APPLICATION OF CHIRAL SPIROCYCLIC PHOSPHINE-NITROGEN-PHOSPHINE TRIDENTATE LIGAND AND IRIDIUM CATALYST THEREOF

(71) Applicant: Zhejiang Jiuzhou Pharmaceutical Co., Ltd., Taizhou (CN)

(72) Inventors: Qilin Zhou, Tianjin (CN); Fenghua Zhang, Tianjin (CN); Jianhua Xie, Tianjin (CN); Lixin Wang, Tianjin (CN)

(*) Notice: Subject to any disclaimer, the term of this patent is extended or adjusted under 35 U.S.C. 154(b) by 323 days.

(21) Appl. No.: 17/783,648

(22) PCT Filed: Dec. 17, 2020

(86) PCT No.: PCT/CN2020/137041
§ 371 (c)(1),
(2) Date: Nov. 21, 2022

(87) PCT Pub. No.: WO2021/139499
PCT Pub. Date: Jul. 15, 2021

(65) Prior Publication Data
US 2023/0151035 A1    May 18, 2023

(30) Foreign Application Priority Data

Jan. 9, 2020  (CN) .......................... 202010012689.5

(51) Int. Cl.
*C07F 9/50* (2006.01)
*B01J 31/18* (2006.01)
(Continued)

(52) U.S. Cl.
CPC ......... *C07F 9/5022* (2013.01); *B01J 31/1805* (2013.01); *B01J 31/2409* (2013.01);
(Continued)

(58) Field of Classification Search
None
See application file for complete search history.

(56) References Cited

U.S. PATENT DOCUMENTS 8,962,839 B2    2/2015 Zhou et al.
10,550,138 B2   2/2020 Zhou et al.

FOREIGN PATENT DOCUMENTS

CN        109970795 A     7/2019

OTHER PUBLICATIONS

English abstract; Chinese Application with Publication No. CN109970795A.

*Primary Examiner* — Yun Qian

(57) ABSTRACT

The present invention relates to a preparation method for and an application of a chiral spirocyclic phosphine-nitrogen-phosphine tridentate ligand SpiroPNP and an iridium catalyst Ir-SpiroPNP thereof. The chiral spirocyclic phosphine-nitrogen-phosphine tridentate ligand is a compound represented by formula I, or a racemate or optical isomer thereof or a catalytically acceptable salt thereof; and the main structural feature is a phosphine ligand having a chiral spiro indene skeleton and a large sterically hindered substituent. The chiral spirocyclic phosphine-nitrogen-phosphine tridentate ligand can be synthesized into a chiral starting material from a 7-diaryl/alkylphosphino-7'-amino-1,1'-spirodihydroindenyl compound having a spiro ring skeleton. The iridium catalyst of the chiral spirocyclic phosphino-7'-amino-1,1'-spirodihydroindenyl compound having a spiro ring skeleton. The iridium catalyst of the chiral spirocyclic phosphine-nitrogen-phosphine tridentate
(Continued)

ligand is a compound represented by formula II, or a racemate or optical isomer thereof, or a catalytically acceptable salt thereof. The iridium catalyst can be used to catalyze the asymmetric catalytic hydrogenation of carbonyl compounds, and especially in the asymmetric catalytic hydrogenation of simple dialkyl ketones. Said catalyst exhibits high yield (>99%) and enantioselectivity (up to 99.8% ee), thus having practical value.

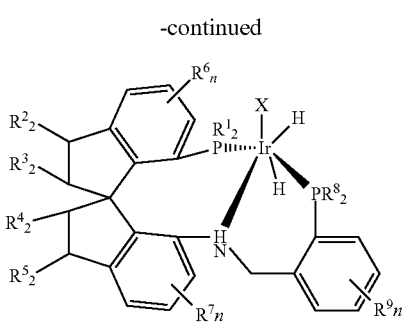

II

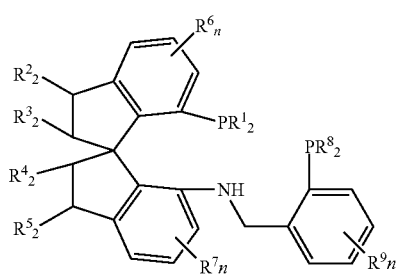

I

12 Claims, 1 Drawing Sheet

(51) Int. Cl.
B01J 31/24 (2006.01)
B01J 37/00 (2006.01)
C07B 53/00 (2006.01)
(52) U.S. Cl.
CPC .......... *B01J 37/00* (2013.01); *B01J 2231/643* (2013.01); *C07B 53/00* (2013.01); *C07B 2200/07* (2013.01)

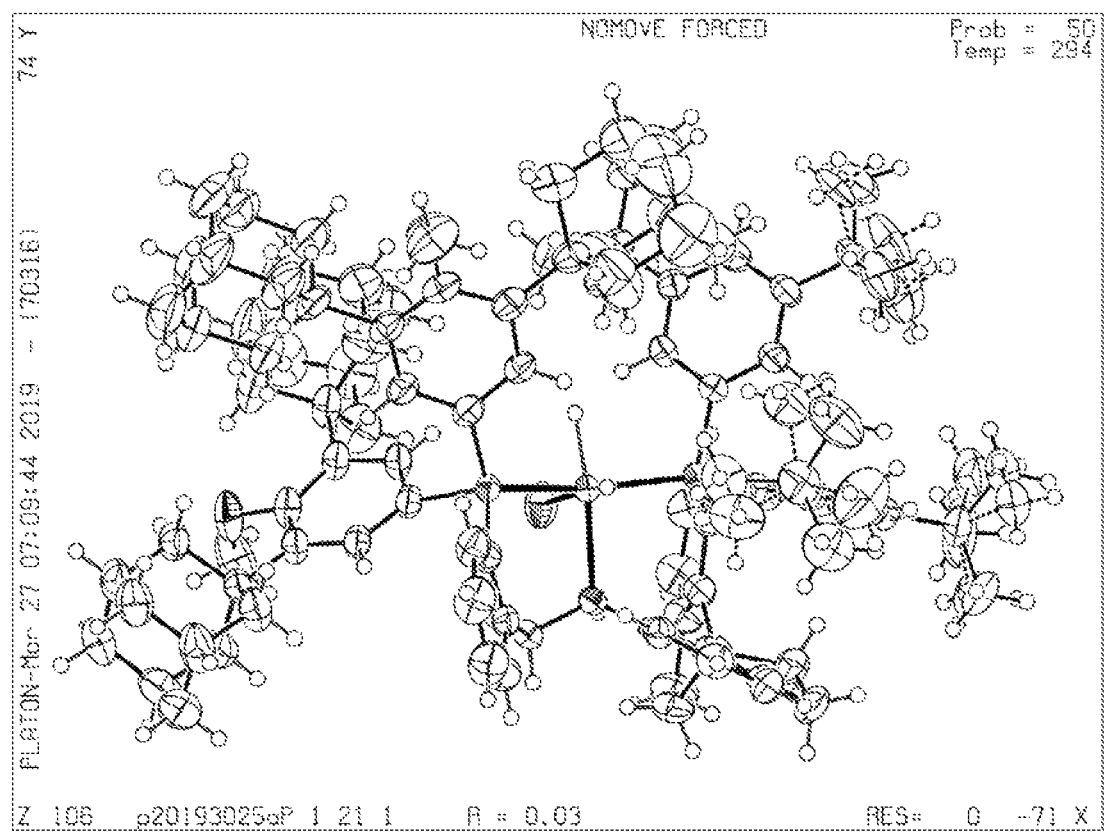

PREPARATION METHOD FOR AND APPLICATION OF CHIRAL SPIROCYCLIC PHOSPHINE-NITROGEN-PHOSPHINE TRIDENTATE LIGAND AND IRIDIUM CATALYST THEREOF

TECHNICAL FIELD

The present invention belongs to organic synthesis technical field, of which relating to chiral spirocyclic phosphine-nitrogen-phosphine tridentate ligands and their iridium catalysts, their preparation methods, uses thereof, and in particular relating to the chiral phosphine-nitrogen-phosphine with spirocyclic skeleton and their iridium catalysts, preparation method thereof and their use in the asymmetric catalytic hydrogenation of simple dialkyl ketones.

BACKGROUND

Using transition metals for asymmetric catalytic hydrogenation has the advantages of high atom economy, mild reaction conditions, high catalytic activity, and good enantioselectivity. The chiral technique has become one of the most simple, convenient and efficient methods to obtain chiral molecules. The chiral technique has also been widely used in the pharmaceutical manufacturing field such as manufacturing chiral pharmaceutical molecules and chiral pesticides, which L-dopa, carbapenicillin, jinduoer and so on listed as examples. It is precisely because of outstanding contributions in the field of chiral control that the Nobel Prize in Chemistry in 2001 was awarded to three professors Konwles, Noyori and Sharpless. The event has demonstrated asymmetric catalytic synthesis technical field has its own importantly scientific significance and its possible far-reaching impact in related fields such as fields of medicine, pesticides, chemicals, materials, etc.

Among several types of unsaturated molecules, ketones are the most easily available type of unsaturated molecules, and their asymmetric catalytic hydrogenation has also received extensive attention from scientists. Scientists have been done the research and developed varieties of catalytic systems to realize the asymmetric catalytic hydrogenation of functionalized ketones and aryl alkyl ketones for more than 40 years' study, of which some of the systems achieving high catalytic efficiency and enantioselectivity, for the reason of the precise recognition by the catalyst to the carbonyl plane of the two types of substrates. Some achievements has been made in the above-mentioned asymmetric catalytic hydrogenation of carbonyl substrates, while other further achievements are also still being of the scientists pursuit and dream, that is further achievements in another type of representative carbonyl substrate, of which having little difference in electrical properties and steric hindrance such as dialkyl ketones. How to realize high enantioselective in hydrogenation reaction for those carbonyl substrates, having not been well realized so far. How to achieve precise control of chirality like enzymes using in asymmetric catalytic hydrogenation of dialkyl ketones such as methyl ethyl ketone with high enantioselective, still remained to be challenging for scientists to some extent. Considering the hydrogenation product are further importantly used in the synthesis of chiral drugs and chiral pesticides, the design and development of new and efficient chiral ligands and catalysts are becoming in demand and great significance work are needed to be made to overcome the difficulty and challenge in the field of asymmetric catalysis research.

For recently years, our research team has been designed and synthesized three types of novel tridentate ligands based on the superior chiral spiro skeleton. The first type is the chiral spirocyclic pyridylaminophosphine tridentate ligand SpiroPAP (Xie, J.-H.; Liu, X.-Y.; Xie, J.-B.; Wang, L.-X.; Zhou, Q.-L. Angew. Chem. Int. Ed. 2011, 50, 7329-9332), its iridium complex Ir-SpiroPAP has a very outstanding performance in the asymmetric catalytic hydrogenation of carbonyl compounds. The selectivity value is 99% ee, and the value of TON can be more than 4.5 million. The iridium catalyst Ir-SpiroPAP of the chiral spirocyclic pyridylaminophosphine tridentate ligand is also very effective for the asymmetric catalytic hydrogenation of β-aryl-β-ketoesters, and can give up to 99% ee of enantioselectivity. The value of TON can be more than 1.23 million (Xie, J.-H.; Liu, X.-Y.; Yang, X.-H.; Xie, J.-B.; Wang, L.-X.; Zhou, Q.-L. Angew. Chem. Int. Ed. 2012, 51, 201-203). The second type is the chiral spirocyclic phosphine-nitrogen-sulfur tridentate ligand SpiroSAP. Its iridium complex Ir-SpiroSAP can obtain excellent performance in the asymmetric catalytic hydrogenation of carbonyl compounds such as β-alkyl-β-ketoesters with enantioselectivity (up to 99.9% ee) and conversion numbers up to 350,000 (Bao, D.-H.; Wu, H.-L.; Liu, C.-L.; Xie, J.-H.; Zhou, Q.-L. Angew. Chem. Int. Ed. 2015, 54, 8791-8794). The third type is the chiral spirocyclic phosphine-amino-oxazoline tridentate SpiroOAP, whose iridium complex can obtain excellent enantioselectivity in the asymmetric catalytic hydrogenation of carbonyl compounds such as α-ketoamides with enantioselectivity (up to 98% ee) and conversion numbers up to 10,000 conversions (Zhang, F.-H.; Wang, C.; Xie, J.-H.; Zhou, Q.-L. Adv. Synth. Catal. 2019, 361, 2832-2835).

There exists the difficulty for carrying out simple dialkyl ketones in asymmetric catalytic hydrogenation reaction to obtain high enantioselective especially such as for carrying out methyl ethyl ketone for the reason of the chirality of the carbonyl plane of the substrate being very difficult to be recognized by the catalyst. So maybe designing a chiral catalyst with huge steric hindrance is the key point for carrying out simple dialkyl ketones in hydrogenation reaction for the reason of it can realize an precise identity for methyl and ethyl group located at the two end of carbonyl group which have almost similar structure property.

SUMMARY OF THE INVENTION

The objective of the present invention is to provide such kind of chiral spirocyclic phosphine-nitrogen-phosphine tridentate ligand, its iridium catalyst, their preparation method thereof, and their use in simple asymmetric catalytic hydrogenation of dialkyl ketones. In asymmetric catalytic hydrogenation of carbonyl compounds, this kind of chiral spirocyclic tridentate ligand has been designed based on the relationship between ligand structure and their catalytic activity and enantioselectivity. The chiral spirocyclic tridentate ligand includes three kinds of ligands such as chiral spirocyclic pyridylaminophosphine tridentate ligand Ir-SpiroPAP, chiral spirocyclic phosphine-nitrogen-sulfur tridentate ligand Ir-SpiroSAP and chiral spirocyclic phosphine-amino-oxazoline tridentate ligand Ir-SpiroOAP. Introducing a new phosphorus atom in the chiral spirocyclic amino phosphine ligand SpiroAP (Xie, J.-B.; Xie, J.-H.; Liu, X.-Y.; Kong, W.-L.; Li, S.; Zhou, Q.-L J Am. Chem. Soc. 2010, 132, 4538-4539. Zhou Qilin, Xie Jianhua, Xie Jianbo, Wang Lixin CN101671365A), the new phosphine-nitrogen-phosphine tridentate ligand can be designed. By introducing different properties substituents in the phosphorus atom, it can easily adjust the steric hindrance around the metal center, thereby significantly improving the chirality control of the catalyst on the substrate.

When it being used as asymmetric catalysis in hydrogenation reaction for carbonyl compounds such as simple dialkyl ketones, the ligand and catalyst can realize excellent enantioselectivity with (up to 99.8% ee) and up to 4300 conversion number (TON), thus a kind of novel and inventive chiral ligands and catalysts product have been provided in the present invention for asymmetric hydrogenation of carbonyl compounds.

The present invention provides chiral spirocyclic phosphine-nitrogen-phosphine tridentate ligand SpiroPNP, having the structure of general formula I or its optical isomer or a racemate thereof, or a catalytically acceptable salt thereof,

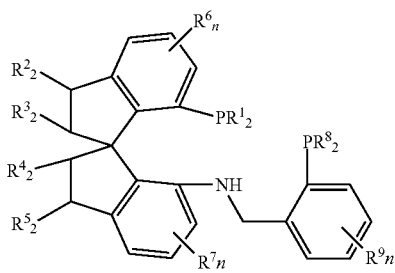

I

The present invention provides chiral spirocyclic phosphine-nitrogen-phosphine tridentate iridium catalyst Ir-SpiroPNP, having the structure of formula II or its optical isomer or a racemate thereof, or a catalytically acceptable salt thereof,

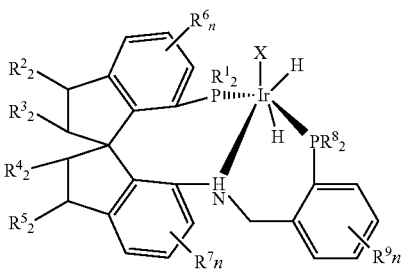

II

Wherein, $R^1$ is selected from C1-C10 hydrocarbyl, phenyl, substituted phenyl, 1-naphthyl, 2-naphthyl, heteroaryl or benzyl, and the substituent on the phenyl group is C1-C10 hydrocarbyl, alkoxy, the number of substituents is 1 to 5, and the heteroaryl is furyl, thienyl or pyridyl;

$R^2$, $R^3$, $R^4$, $R^5$ are independently selected from H, C1~C10 alkyl, phenyl, substituted phenyl, 1-naphthyl, 2-naphthyl, heteroaryl or benzyl, and the substituent on said substituted phenyl is C1-C10 hydrocarbyl or alkoxy, with a substituent amount of 1-5, and said heteroaryl is furyl, thienyl or pyridyl; or C1-C10 alkoxy; or $R^2$~$R^3$, $R^4$~$R^5$ are incorporated into C3~C7 aliphatic ring or aromatic ring; $R^2$, $R^3$, $R^4$, $R^5$ can be the same or different;

$R^6$ and $R^7$ are independently selected from H, C1~C10 alkyl, C1~C10 alkoxy, C1~C10 aliphatic amido group, and n=0~3; or when n≥2, two adjacent $R^6$ groups or two adjacent $R^7$ groups can be incorporated into C3-C7 aliphatic ring or aromatic ring, and $R^6$, $R^7$ can be the same or different;

$R^8$, $R^9$ are H, $C_1$-$C_{10}$ alkyl, $C_1$-$C_{10}$ alkoxy, phenyl, substituted phenyl, 1-naphthyl, 2-naphthyl, heteroaryl or benzyl, and the substituent on said substituted phenyl is $C_1$-$C_{10}$ alkyl or alkoxy, with a substituent amount of 1-5, and said heteroaryl is furyl, thienyl or pyridyl, and adjacent $R^8$ and $R^9$ groups can be incorporated into rings through the C2-C4 carbon chain and carbon chains containing nitrogen atom, oxygen atom or sulfur atom, or through aromatic rings, or heteroaromatic rings, and $R^8$, $R^9$ can be the same or different.

X can be common anions such as Cl$^-$, Br$^-$, OMe$^-$, BF$_4^-$, OTf$^-$.

The present invention provides the method for synthesizing the chiral spirocyclic phosphine-nitrogen-phosphine tridentate ligand SpiroPNP and its iridium catalyst Ir-SpiroPNP. The preparation method is performed via the following reaction steps,

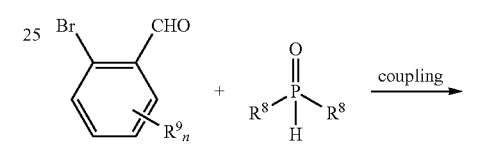

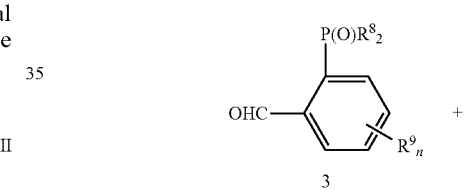

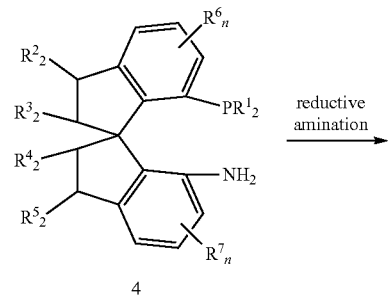

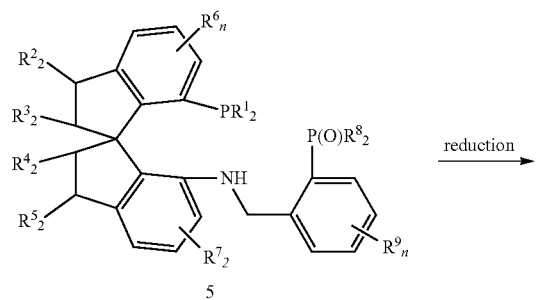

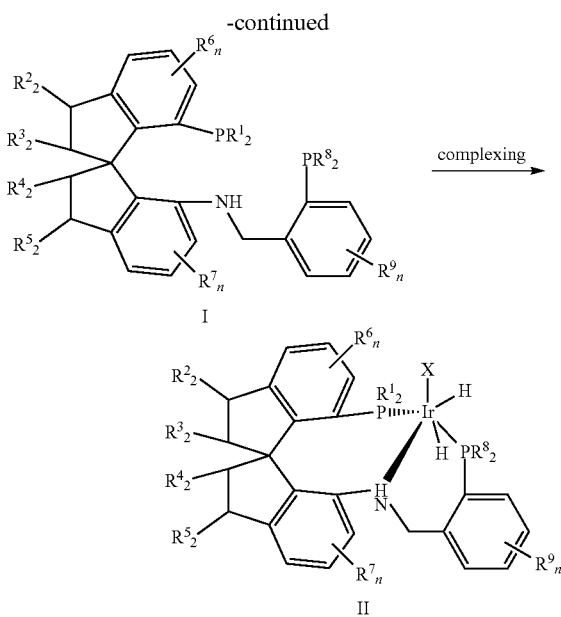

Wherein, the definition of $R^1 \sim R^9$ and X can be defined as above. The compound represented by formula 4 with a chiral spirodihydroindene skeleton is prepared according to literature methods' disclosure (J.-B. Xie, J.-H. Xie, X.-Y. Liu, W.-L. Kong, S. Li, Q.-L. Zhou, J. Am. Chem. Soc. 2010, 132, 4538; Zhou Qilin, Xie Jianhua, Xie Jianbo, Wang Lixin, CN 101671365A).

The method for synthesizing the chiral spirocyclic phosphine-nitrogen-phosphine tridentate ligand SpiroPNP and its iridium catalyst Ir-SpiroPNP comprising the following steps:

First in the presence of organic solvent, base and palladium catalyst, reacting the compound represented by formula 1 with the compound represented by formula 2 in a reactor for 12 to 24 hours to prepare the compound represented by formula 3.

In the presence of a reducing agent, the compound represented by formula 3 and the compound represented by formula 4 undergo reductive amination obtaining the compound represented by formula 5.

In the presence of an organic solvent and a reducing agent, the compound represented by formula 5 undergo reduction reaction obtaining the compound represented by formula I.

The compound represented by formula I complexing with iridium catalyst precursors in an organic solvent obtaining the compound represented by formula II.

In the preparation method defined as above, the said organic solvent is selected from the single or mixture solvents of methanol, ethanol, propanol, isopropanol, butanol, tetrahydrofuran, toluene, xylene, methyl tert-butyl ether, diethyl ether, dioxane, N,N-dimethylformamide, dimethyl sulfoxide, dichloromethane, chloroform or 1,2-dichloroethane; the reducing reagent is lithium aluminum hydride, sodium borohydride, sodium triacetoxyborohydride, sodium nitrile borohydride, trichlorosilane or phenylsilane; said base maybe organic base or inorganic base, said organic base maybe pyridine, triethylamine, tributyl amine, N-methylmorpholine or N,N-diethylisopropylamine; said inorganic base maybe sodium hydroxide, potassium hydroxide, sodium carbonate or potassium carbonate; said palladium catalyst maybe palladium acetate or palladium on carbon; said iridium catalyst maybe 1,5-cyclooctadiene iridium chloride dimer or bis(1,5-cyclooctadiene)di-methoxy-diiridium.

The said application of the chiral spirocyclic phosphine-nitrogen-phosphine tridentate ligand and its iridium catalyst in the present invention, that is separately using as a ligand and catalyst for the asymmetric catalytic hydrogenation reaction of simple dialkyl ketones and other carbonyl compounds.

As a preferable proposal, first, the said chiral spirocyclic phosphine-nitrogen-phosphine tridentate ligand is complexed with the transition metal to synthesize coordination compound, then the synthesized coordination compound is used in the asymmetric catalytic hydrogenation of carbonyl compounds such as simple dialkyl ketones.

As a preferable proposal, the preparation method of the chiral catalyst complex of the chiral spirocyclic phosphine-nitrogen-phosphine tridentate ligand with transition metal salt comprising the following forming steps: under the condition of inert gas atmosphere, adding the chiral spirocyclic phosphine-nitrogen-phosphine tridentate ligand and a transition metal salt into an organic solvent, at the temperature of 70-100° C. and 0.1-20 atm hydrogen atmosphere, reacting the mixture with stirring for 10-24 hours to obtain the chiral catalyst required for the hydrogenation reaction.

As a further preferable proposal, the molar ratio of the chiral spirocyclic phosphine-nitrogen-phosphine tridentate ligand and transition metal salt is 1:1~2:1, more preferable, is 1.2:1~1.8:1.

As a further preferable proposal, the said transition metal is iridium transition metal. The said iridium catalyst precursor maybe [Ir(COD)Cl]$_2$(COD=cyclooctadiene), [Ir(COD)$_2$]BF$_4$, [Ir(COD)$_2$]PF$_6$, [Ir(COD)$_2$]SbF$_6$, or [Ir(COD)$_2$]OTf.

As a further preferred solution, the organic solvent is the single or mixtures of the solvents selected from methanol, ethanol, propanol, isopropanol, butanol, tetrahydrofuran, toluene, methyl tert-butyl ether, 1,4-dioxane, N,N-dimethyl formamide or dimethyl sulfoxide.

As a further preferred solution, the preparation method of chiral alcohol compounds, comprising the steps of, in the presence of organic solvent, the said coordination compound which has been prepared is used as the chiral catalyst, for catalyzing the substrate carbonyl compound's reaction under the condition of base and at the hydrogen atmosphere condition of the value range of 0.1-100 atm at a temperature of 0 to 80° C. to obtain chiral alcohol compounds.

The molar ratio of the carbonyl substrate to the catalyst is 100:1 to 500,000:1; the concentration of the substrate is 0.001 to 10.0M; The alkali concentration is 0.005M to 1.0M.

Said base is selected from sodium hydroxide, potassium hydroxide, sodium carbonate, potassium carbonate, sodium ethoxide, potassium ethoxide, sodium tert-butoxide, potassium tert-butoxide, lithium tert-butoxide, triethylamine, tributylamine or N-methylmorpholine.

As a further preferred solution, the chiral spirocyclic phosphine-nitrogen-phosphine tridentate ligand is selected from the following compounds or its optical isomer or racemate thereof, or a catalytically acceptable salt thereof:

Ia
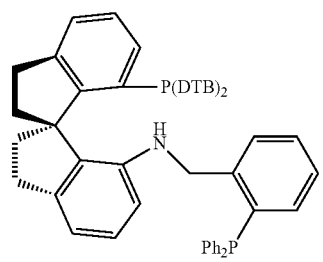
Ib
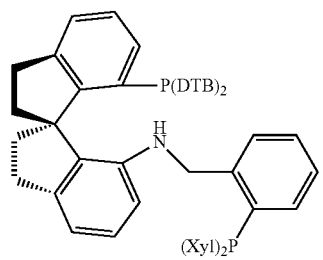
Ic
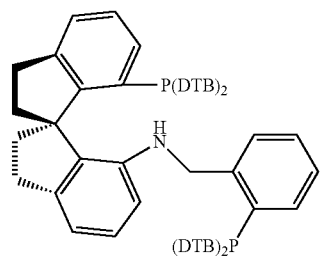
Id
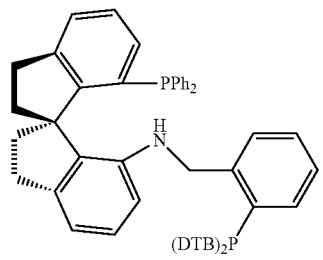
Ie
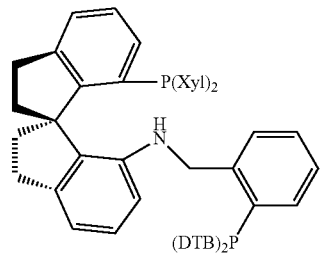
If
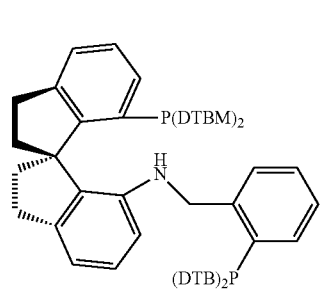
-continued
Ig
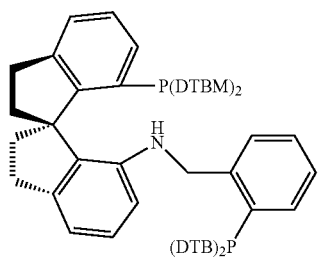
Ih
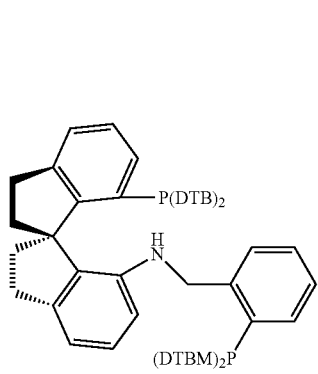
Ii
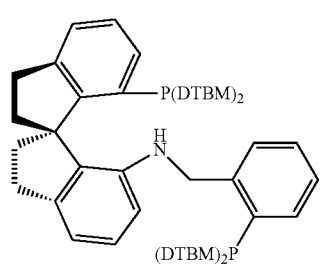
Ij
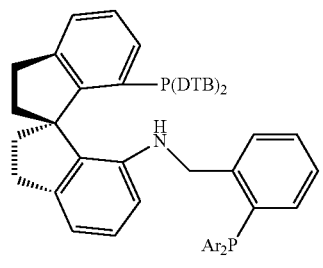
Ik
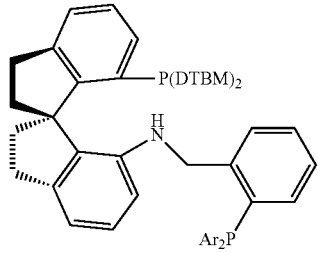

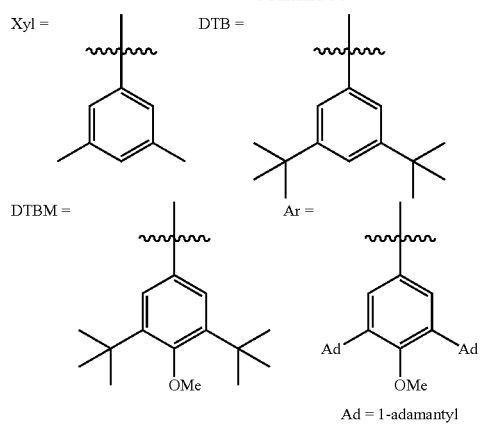

Ad = 1-adamantyl

As a further preferred solution, the chiral spirocyclic phosphine-nitrogen-phosphine tridentate ligand iridium catalyst is selected from the following compounds or its optical isomer or racemate thereof, or a catalytically acceptable salt thereof:

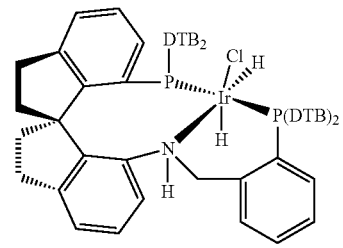

IIa

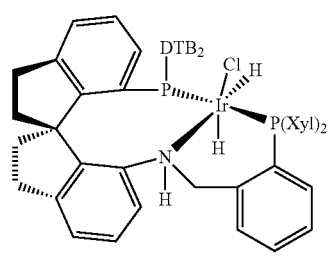

IIb

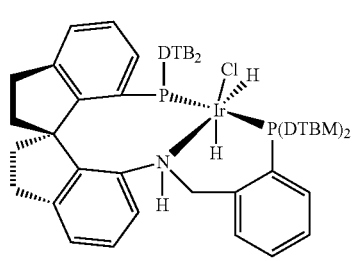

IIc

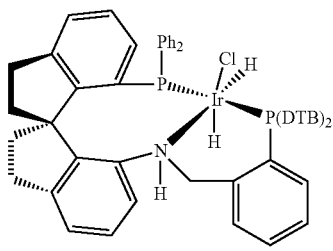

IId

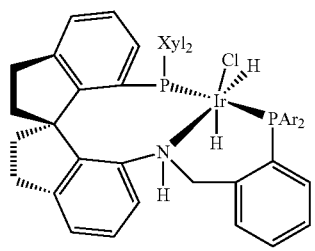

IIe

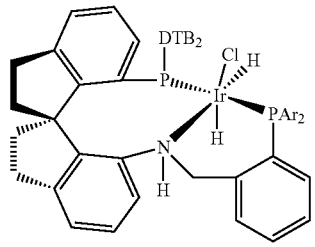

IIf

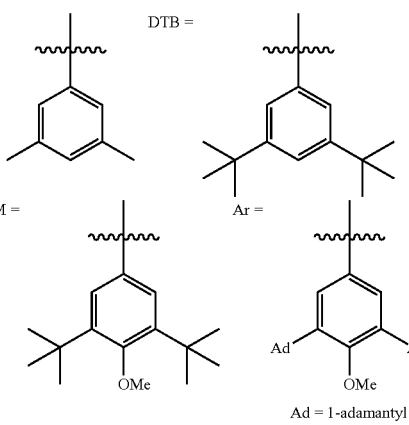

Ad = 1-adamantyl

The chiral spirocyclic phosphine-nitrogen-phosphine tridentate ligand provided by the present invention has the main structural property of a phosphine ligand with a chiral spirodihydroindene skeleton and a large sterically hindered substituent, which can be used as a chiral ligand in the iridium catalyzed asymmetric catalytic hydrogenation reaction of carbonyl compounds such as simple dialkyl ketones. That is, its iridium catalyst has achieved high yield (>99%) and enantioselectivity in the asymmetric hydrogenation reaction of simple dialkyl ketones with enantioselectivity (up to 99.8% ee). Compared with the prior art, the present invention has the following remarkable effects:

1) The chiral spirocyclic phosphine-nitrogen-phosphine tridentate ligand provided by the present invention, being complexed with a transition metal salt to form complex, later is used in the asymmetric hydrogenation reaction of carbonyl compounds such as simple dialkyl ketones. It has excellent enantioselectivity and high catalytic activity.
2) The preparation method of the chiral spirocyclic phosphine-nitrogen-phosphine tridentate ligand and its iridium catalyst provided by the present invention is simple in operation, and is particularly suitable for asymmetric catalytic hydrogenation of carbonyl compounds. The reaction is carried out in mild reaction conditions with high efficiency, and is suitable for large-scale production. It can be operable and practical in commercial industry use.
3) The present invention provides a variety of chiral dialkyl alcohols with important biological activity. These chiral dialkyl alcohols are widely used in the synthetic industrial field for synthesizing pharmaceutical molecules and have great practical value.

DETAILED EMBODIMENT

Hereinafter, the present invention will be further described in detail by the incorporation of the examples. The listed examples will help to understand the present invention, but cannot limit the content of the present invention.

Example 1

Synthetic Route of Ligand Ia:

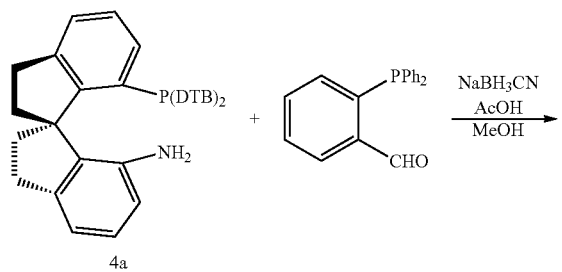

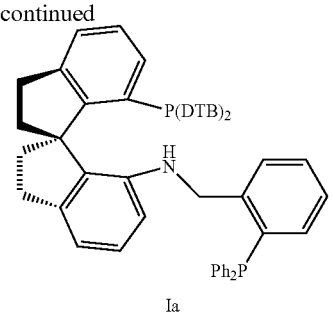

Ia

In an argon atmosphere, into a 100 mL dry Schlenk tube, (R)-7'-bis-(3,5-di-tert-butylphenyl)phosphino-7'-amino-1,1'-spiroindene 4a (300 mg, 0.46 mmol) was weighed and placed, 12 mL of anhydrous methanol was injected into by the syringe, and the mixture was stirred to dissolve. Adding 2-diphenylphosphine benzaldehyde (176 mg, 0.61 mmol) and glacial acetic acid (42 µL) into the dry Schlenk tube. The reaction was stirred and reacted at room temperature for 3 hours. Open the reverse plug, pouring NaBH$_3$CN (87 mg, 1.38 mmol) into the mixture at one time, and reacting at 40° C. for 15 hours. After the reaction was completed, it was cooled to room temperature, the system was spin-dried, and dichloromethane was added to dissolve, and it was quenched with saturated sodium bicarbonate solution. The quenched solution was extracted with dichloromethane and the layered organic phases were combined and dried with anhydrous magnesium sulfate. The desiccant was removed by suction filtration, and the filtrate was evaporated to remove the solvent with a rotary evaporator. The residue was purified by silica gel column chromatography (petroleum ether:ethyl acetate=30:1) to obtain 342 mg of white solid Ia with a yield of 80%.

Data for Ia:

White solid, melting point 80-82° C., $[\alpha]_D^{20}$ 167.2 (c, 0.5, CHCl$_3$).

| | |
|---|---|
| $^1$H NMR (400 MHz, CDCl$_3$) | δ 7.37-7.25 (m, 6H), 7.25-7.22 (m, 3H), 7.22-7.14 (m, 5H), 7.11 (dd, J = 7.0, 4.1 Hz, 1H), 7.08-6.98 (m, 3H), 6.94-6.82 (m, 3H), 6.82-6.73 (m, 3H), 6.63 (d, J = 7.3 Hz, 1H), 6.06 (d, J = 7.9 Hz, 1H), 4.32-4.15 (m, 1H), 3.80 (dd, J = 15.8, 5.4 Hz, 1H), 3.66 (t, J = 5.3 Hz, 1H), 3.14-2.78 (m, 3H), 2.69 (dd, J = 15.6, 9.1 Hz, 1H), 2.38 (dd, J = 21.2, 11.7 Hz, 1H), 2.18-1.85 (m, 3H), 1.16 (s, 18H), 1.10 (s, 18H). |
| $^{13}$C NMR (101 MHz, CDCl$_3$) | δ 152.28 (d, J = 24.3 Hz), 149.82 (dd, J = 6.3, 1.7 Hz), 144.15 (t, J = 3.1 Hz), 143.97 (d, J = 7.1 Hz), 143.67 (d, J = 22.6 Hz), 137.76 (d, J = 11.6 Hz), 136.50 (dd, J = 11.1, 3.0 Hz), 136.24 (d, J = 13.2 Hz), 135.27 (d, J = 23.7 Hz), 134.60 (d, J = 15.3 Hz), 133.81 (dd, J = 19.8, 9.4 Hz), 133.41 (d, J = 1.8 Hz), 133.20 (s), 131.88 (d, J = 3.3 Hz), 129.02 (s), 128.70 (s), 128.63-128.36 (m), 128.28 (d, J = 10.2 Hz), 128.13 (s), 127.93 (s), 126.74 (d, J = 23.6 Hz), 126.35 (d, J = 5.2 Hz), 125.69 (s), 121.74 (d, J = 41.3 Hz), 113.60 (s), 108.52 (s), 61.57 (d, J = 3.3 Hz), 45.28 (d, J = 27.1 Hz), 38.31 (d, J = 3.3 Hz), 36.20 (s), 34.69 (s), 31.33 (d, J = 4.7 Hz). |
| $^{31}$P NMR (162 MHz, CDCl$_3$) | δ −16.84 (s), −17.93 (s). |
| HR-MS (MALDI) | Calcd for C$_{64}$H$_{73}$NP$_2$ [M + H]$^+$: 918.5291; Found: 918.5295. |

Example 2

Synthetic Route of Ligand Ib:

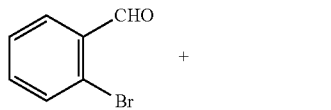

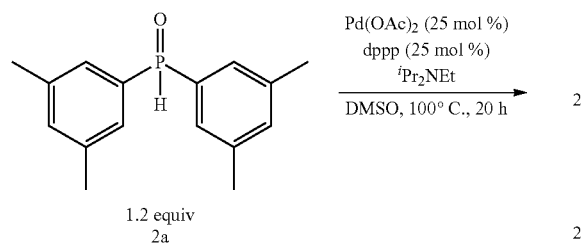

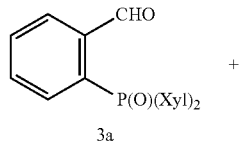

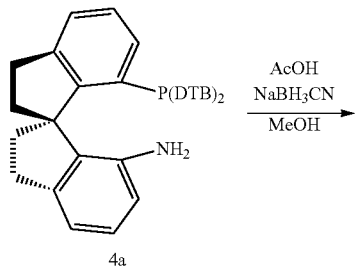

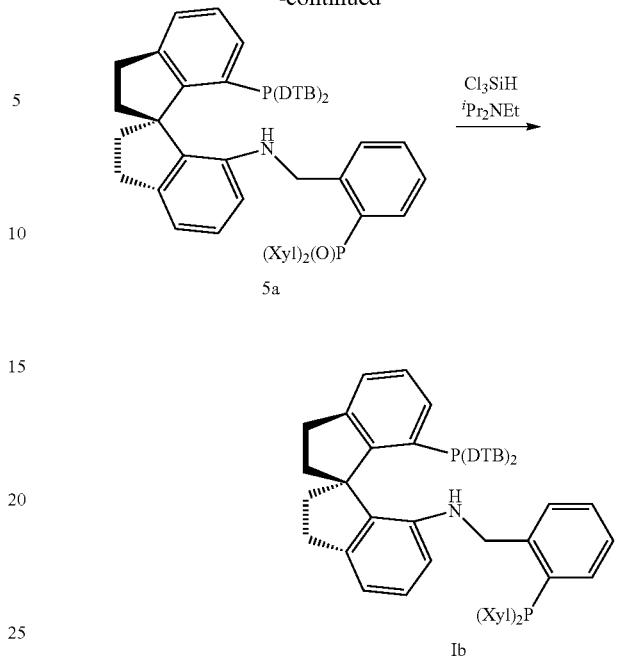

Synthesis of Intermediate 3a:

Into a 25 mL Schlenk tube, Pd(OAc)$_2$ (56 mg), dppp, namely 1,3-bis(diphenylphosphine)propane (103 mg), 2a (310 mg) was weighed, replacing the tube air with argon, and pouring the degassed DMSO (4.0 mL) into the tube, stir evenly, adding o-bromobenzaldehyde (118 μL) and diisopropylethylamine (248 μL), and heating the reaction in an oil bath to 100° C. for 20 hours. After the reaction was finished, the reaction mixture was cooled to room temperature. Adding 10 mL ethyl acetate and 10 mL water into the reaction mixture. And then it was extracted with ethyl acetate, and the organic phases were combined and dried with anhydrous magnesium sulfate. The desiccant was removed by suction filtration, and the filtrate was evaporated to remove the solvent with a rotary evaporator. The residue was purified by silica gel column chromatography (petroleum ether:ethyl acetate=5:1) to obtain 242 mg of white solid 3a with a yield of 66%.

Data for Intermediate 3a:
White solid, melting point 202-204° C.

| | |
|---|---|
| $^1$H NMR (400 MHz, CDCl$_3$) | δ 10.74 (s, 1H), 8.15 (dd, J = 7.3, 3.1 Hz, 1H), 7.67 (t, J = 7.5 Hz, 1H), 7.55 (ddd, J = 7.5, 5.9, 1.7 Hz, 1H), 7.32-7.16 (m, 7H), 2.33 (s, 12H). |
| $^{13}$C NMR (101 MHz, CDCl$_3$) | δ 191.49 (d, J = 5.8 Hz), 139.45 (d, J = 6.5 Hz), 138.49 (d, J = 13.1 Hz), 135.73 (d, J = 94.8 Hz), 134.07 (d, J = 2.8 Hz), 133.63 (d, J = 11.1 Hz), 132.85-132.40 (m), 132.10 (d, J = 2.3 Hz), 131,56 (s), 129.38 (d, J = 9.9 Hz), 128.69 (d, J = 8.8 Hz), 21.28 (s). |
| $^{31}$P NMR (162 MHz, CDCl$_3$) | δ 31.46. |
| HR-MS (MALDI) | Calcd for C$_{23}$H$_{23}$O$_2$P [M + H]$^+$: 363.1508; Found: 363.1512. |

Synthesis of Intermediate 5a:

In an argon atmosphere, (R)-7'-bis-(3,5-di-tert-butylphenyl)phosphino-7'-amino-1,1'-spiroindene 4a (273 mg, 0.42 mmol) was weighed and placed into a 100 mL dry Schlenk tube, 12 mL of anhydrous methanol was injected by the syringe. The mixture was stirred to dissolve. Adding 3a (200 mg, 0.55 mmol) and glacial acetic acid (32 µL, 0.55 mmol) into. The reaction mixture was reacted and stirred at room temperature for 3 hours. Open the reverse plug, was added NaBH$_3$CN (160 mg, 2.52 mmol) in portion, and reacted at 40° C. for 15 hours. Upon completion of the reaction, the reaction mixture was cooled to room temperature, the system was spin-dried, and dichloromethane was added to dissolve, and it was quenched with saturated sodium bicarbonate solution. The reaction mixture was further extracted with dichloromethane, and the organic phases were combined and dried with anhydrous magnesium sulfate. The desiccant was removed by suction filtration, and the filtrate was evaporated to remove the solvent with a rotary evaporator. The residue was purified by silica gel column chromatography (petroleum ether:ethyl acetate=3:1) to obtain 398 mg of white solid 5a, with a yield of 95%.

Data for Intermediate 5a:

White solid, melting point is 118-120° C., $[\alpha]_D^{20}$ 98.4 (c, 0.5, CHCl$_3$).

| | |
|---|---|
| $^1$H NMR (400 MHz, CDCl$_3$) | δ 7.38-7.23 (m, 8H), 7.21-7.06 (m, 7H), 7.02 (t, J = 7.7 Hz, 1H), 6.96 (dd, J = 8.0, 1.8 Hz, 2H), 6.86 (dd, J = 7.3, 1.7 Hz, 2H), 6.61 (d, J = 7.4 Hz, 1H), 5.87 (d, J = 7.9 Hz, 1H), 4.67 (dd, J = 17.0, 5.9 Hz, 1H), 4.12 (dd, J = 17.5, 5.8 Hz, 1H), 3.74 (t, J = 5.6 Hz, 1H), 3.16-2.88 (m, 2H), 2.87-2.73 (m, 1H), 2.52 (dd, J = 15.6, 9.3 Hz, 1H), 241-2.24 (m, 13H), 2.03 (dd, J = 12.8, 7.2 Hz, 1H), 1.94 (dd, J = 13.1, 8.5 Hz, 1H), 1.71 (dd, J = 22.6, 9.9 Hz, 1H), 1.24 (s, 18H), 1.12 (s, 18H). |
| $^{13}$C NMR (101 MHz, CDCl$_3$) | δ 151.70 (d, J = 24.0 Hz), 149.96 (d, J = 7.0 Hz), 149.70 (d, J = 5.3 Hz), 144.59 (d, J = 4.2 Hz), 144.19 (d, J = 1.7 Hz), 143.82 (d, J = 6.7 Hz), 138.10 (dd, J = 12.4, 10.8 Hz), 137.18-136.64 (m), 135.38 (d, J = 24.1 Hz), 133.64 (dd, J = 4.9, 2.6 Hz), 133.37 (d, J = 12.1 Hz), 133.02 (d, J = 12.4 Hz), 132.54 (s), 132.00 (d, J = 11.9 Hz), 131.11 (d, J = 2.5 Hz), 129.91 (s), 129.39 (dd, J = 15.2, 9.8 Hz), 129.12 (s), 128.90 (s), 127.93 (d, J = 34.0 Hz), 127.68-127.26 (m), 126.85 (s), 125.70 (s), 125.60 (s), 121.78 (d, J = 53.7 Hz), 113.39 (s), 108.13 (s), 61.53 (d, J = 2.8 Hz), 45.82 (d, J = 4.6 Hz), 37.47 (s), 36.53 (s), 34.67 (d, J = 7.4 Hz), 31.29 (d, J = 3.6 Hz), 30.78 (d, J = 40.6 Hz), 21.29 (d, J = 2.8 Hz). |
| $^{31}$P NMR (162 MHz, CDCl$_3$) | δ 32.16, -15.24. |
| HR-MS (MALDI) | Calcd for C$_{68}$H$_{81}$NOP$_2$ [M + H]$^+$: 990.5866; Found: 990.5869. |

Synthesis of Ligand Ib:

A 100 mL sealed tube was charged with 5a (348 mg, 0.35 mmol), the tube air was replaced with argon, was added toluene (15 mL) and diisopropylethylamine (581 µL, 3.5 mmol), then at the temperature of 0° C. was added trichlorosilane (354 µL) slowly into the reaction system by dripping, after dripping, the reaction mixture was reacted in an oil bath at 120° C. for 24 hours. After the reaction, the reaction mixture was quenched with 12N sodium hydroxide solution at 0° C., and was extracted with ethyl acetate, the organic phases were combined, and the organic phases were dried with anhydrous magnesium sulfate. The desiccant was removed by suction filtration, and the filtrate was evaporated to remove the solvent with a rotary evaporator. The residue was purified by silica gel column chromatography (petroleum ether:ethyl acetate=30:1) to obtain 130 mg of white solid Ib, with a yield of 37%.

Data for Ib:

White solid, melting point 87-89° C., $[\alpha]_D^{20}$ 142.0 (c, 0.5, CHCl$_3$).

| | |
|---|---|
| $^1$H NMR (400 MHz, CDCl$_3$) | δ 7.25-7.22 (m, 3H), 7.18 (t, J = 7.4 Hz, 1H), 7.13-7.06 (m, 1H), 7.03 (t, J = 7.7 Hz, 3H), 6.94 (s, 3H), 6.87 (d, J = 7.7 Hz, 2H), 6.80 (t, J = 6.1 Hz, 7H), 6.62 (d, J = 7.4 Hz, 1H), 6.06 (d, J = 7.9 Hz, 1H), 4.20 (d, J = 15.7 Hz, 1H), 3.88 (dd, J = 16.0, 5.4 Hz, 1H), 3.71 (t, J = 5.2 Hz, 1H), 2.95 (ddt, J = 32.3, 17.4, 12.8 Hz, 3H), 2.68 (dd, J = 15.6, 9.2 Hz, 1H), 2.49-2.33 (m, 1H), 2.24 (s, 12H), 2.17-2.03 (m, 2H), 1.96 (dd, J = 22.2, 10.0 Hz, 1H), 1.17 (s, 18H), 1.11 (s, 18H). |
| $^{13}$C NMR (101 MHz, CDCl$_3$) | δ 152.25 (d, J = 24.3 Hz), 149.82 (t, J = 5.8 Hz), 144.23 (d, J = 3.6 Hz), 144.14 (d, J = 2.5 Hz), 143.94 (d, J = 7.0 Hz), 143.65 (d, J = 22.4 Hz), 137.92-137.53 (m), 136.45 (s), 136.31 (s), 136.21 (d, J = 2.3 Hz), 136.12 (s), 135.40 (s), 135.11 (d, J = 10.6 Hz), 134.91 (s), 133.37 (s), 133.27 (s), 131.74 (d, J = 3.3 Hz), 131.62 (d, J = 4.8 Hz), 131.42 (d, J = 4.9 Hz), 130.45 (d, J = 14.4 Hz), 128.60 (d, J = 36.4 Hz), 128.21 (s), 127.95 (d, J = 20.8 Hz), 126.67 (d, J = 36.3 Hz), 126.17 (d, J = 5.2 Hz), 125.66 (s), 121.71 (d, J = 27.1 Hz), 113.45 (s), 108.52 (s), 61.61 (d, J = 3.3 Hz), 45.35 (d, J = 26.8 Hz), 38.29 (s), 36.21 (s), 34.69 (d, J = 2.2 Hz), 31.33 (d, J = 3.2 Hz), 30.90 (d, J = 38.2 Hz), 21.30 (s). |
| $^{31}$P NMR (162 MHz, CDCl$_3$) | δ -16.76, -17.76. |
| HR-MS (MALDI) | Calcd for C$_{68}$H$_{81}$NP$_2$ [M + H]$^+$: 974.5917: Found: 974.5922. |

Example 3

Synthetic Route of Ligand Ic:

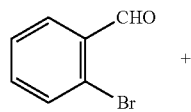

+

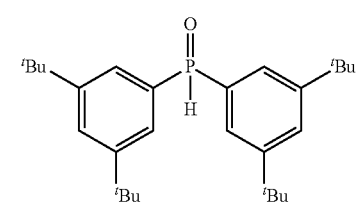

1.2 equiv
2b

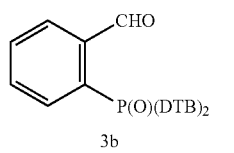

3b

+

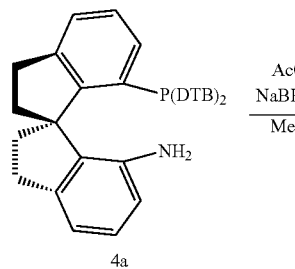

4a

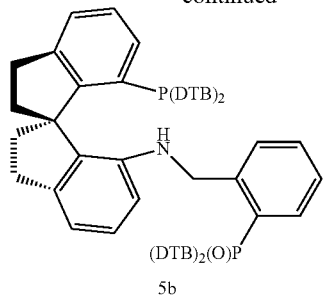

5b

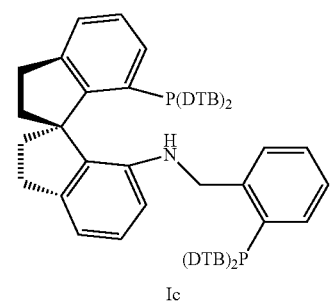

Ic

Synthesis of Intermediate 3b:

A 25 mL sealed tube was charged with Pd(OAc)$_2$ (112 mg), dppp (206 mg) and 2b (1026 mg, 2.4 mmol). The tube air was replaced with Argon. Was added degassed DMSO (8.0 mL), 2-bromobenzaldehyde (234 μL) and $^i$Pr$_2$NEt (496 μL) sequentially. The mixture was stirred at 100° C. by oil bath for 20 h. Upon completion, the reaction mixture was cooled to room temperature and diluted with EtOAc (20 mL) and H$_2$O (30 mL). The resulting mixture was extracted with EtOAc. The combined organic layers were dried over anhydrous MgSO$_4$ and the desiccant was removed by suction filtration and the solvent was evaporated. The residue was purified by silica gel column chromatography (petroleum ether:ethyl acetate=5:1), affording 752 mg of white solid 3b with 71% yield.

Data for Intermediate 3b:
white solid, melting point 58-60° C.

| | |
|---|---|
| $^1$H NMR (400 MHz, CDCl$_3$) | δ 10.79 (s, 1H), 8.15 (dd, J = 7.5, 3.2 Hz, 1H), 7.66 (t, J = 7.6 Hz, 1H), 7.61 (s, 2H), 7.55 (t, J = 7.4 Hz, 1H), 7.45 (d, J = 13.0 Hz, 4H), 7.29-7.20 (m, 1H), 1.26 (s, 36H). |
| $^{13}$C NMR (101 MHz, CDCl$_3$) | δ 191.52 (d, J = 5.5 Hz), 151.22 (d, J = 12.0 Hz), 139.45 (d, J = 6.4 Hz), 136.32 (d, J = 94.0 Hz), 133.41 (d, J = 10.7 Hz), 132.44 (d, J = 11.7 Hz), 131.92 (d, J = 3.2 Hz), 130.90 (s), 128.41 (d, J = 8.8 Hz), 126.15 (d, J = 2.6 Hz), 126.02 (d, J = 10.7 Hz), 34.93 (s), 31.15 (s). |
| $^{31}$P NMR (162 MHz, CDCl$_3$) | δ 32.83. |
| HR-MS (MALDI) | Calcd for C$_{35}$H$_{47}$O$_2$P [M + H]$^+$: 531.3386; Found: 531.3390. |

Synthesis of Intermediate 5b:

Under argon atmosphere, in a 100 mL dry Schlenk tube was charged (R)-7'-bis-(3,5-di-tert-butylphenyl)phosphino-7'-amino-1,1'-spiroindene 4a (550 mg, 0.86 mmol), was added MeOH (12 mL) by injection. Was added 3b (601 mg, 1.13 mmol) and AcOH (64 μL, 1.13 mmol) to the suspension. The mixture was stirred at room temperature for 3 h. Open the anti-port plug, was added NaBH$_3$CN (323 mg, 5.16 mmol) in portion. The reaction mixture was reacted at 40° C. for 15 h. After the reaction was completed, it was cooled to room temperature, the system was spin-dried, was added dichloromethane to dissolve and the mixture was quenched with saturated sodium bicarbonate solution. The resulting mixture was extracted with CH$_2$Cl$_2$. The combined organic layer was dried over MgSO$_4$ and the desiccant was removed by suction filtration and solvent was evaporated. The residue was purified by silica gel column chromatography, affording 980 mg of white solid 5b with 99% yield.

Data for Intermediate 5b:

White solid, melting point 136-138° C., $[\alpha]_D^{20}$ 99.6 (c, 0.5, CHCl$_3$).

| | |
|---|---|
| $^1$H NMR (400 MHz, CDCl$_3$) | δ 7.57 (s, 2H), 7.40 (t, J = 12.0 Hz, 5H), 7.31 (s, 1H), 7.26-6.98 (m, 7H), 6.93 (t, J = 9.2 Hz, 3H), 6.81 (d, J = 6.8 Hz, 2H), 6.54 (d, J = 7.1 Hz, 1H), 5.83 (d, J = 7.7 Hz, 1H), 4.86 (d, J = 13.2 Hz, 1H), 4.20 (d, J = 16.6 Hz, 1H), 3.78 (s, 1H), 2.94 (p, J = 16.1 Hz, 2H), 2.80-2.57 (m, 1H), 2.33 (dt, J = 21.1, 10.0 Hz, 2H), 1.96 (d, J = 17.4 Hz, 1H), 1.83 (t, J = 10.5 Hz, 1H), 1.55 (q, J = 10.3 Hz, 1H), 1.25 (s, 36H), 1.20 (s, 18H), 1.08 (s, 18H) |
| $^{13}$C NMR (101 MHz, CDCl$_3$) | δ 151.34 (d, J = 23.7 Hz), 150.87 (dd, J = 18.0, 11.9 Hz), 149.98 (d, J = 7.5 Hz), 149.69 (d, J = 5.2 Hz), 144.96 (d, J = 3.9 Hz), 144.78 (d, J = 7.6 Hz), 144.23 (s), 143.84 (d, J = 6.4 Hz), 137.12 (d, J = 14.2 Hz), 136.71 (d, J = 11.2 Hz), 135.41 (d, J = 24.1 Hz), 133.39 (d, J = 11.9 Hz), 132.52 (s), 132.47 (s), 132.14 (s), 131.47 (d, J = 5.3 Hz), 130.77 (d, J = 2.4 Hz), 130.05 (s), 129.31 (d, J = 22.2 Hz), 129.06 (s), 128.04 (s), 127.66 (d, J = 18.8 Hz), 127.37 (dd, J = 9.5, 5.7 Hz), 126.83 (s), 126.25 (d, J = 10.5 Hz), 125.93 (s), 125.83 (s), 125.75 (s), 125.52 (s), 125.37 (d, J = 12.5 Hz), 122.17 (s), 121.34 (s), 113.30 (s), 107.93 (s), 61.50 (d, J = 2.8 Hz), 45.99 (d, J = 4.6 Hz), 37.01 (s), 36.67 (s), 34.95 (s), 34.68 (d, J = 6.2 Hz), 31.30 (d, J = 1.2 Hz), 30.76 (d, J = 38.9 Hz). |
| $^{31}$P NMR (162 MHz, CDCl$_3$) | δ 34.68, −13.84. |
| HR-MS (MALDI) | Calcd for C$_{80}$H$_{105}$NOP$_2$ [M + H]$^+$: 1158.7744; Found: 1158.7748. |

Synthesis of Ligand Ic:

In to a 100 mL sealed tube was charged 5b (880 mg, 0.76 mmol), the tube air was replaced with argon, was added toluene (25 mL) and diisopropylethylamine (1.3 mL, 7.6 mmol), At 0° C., trichlorosilane (775 μL) was slowly added dropwise to the reaction system, and after dropping, the reaction was heated in an oil bath at 120° C. for 24 hours. Upon completion of the reaction, the reaction mixture was quenched with 12N sodium hydroxide solution at 0° C., and was extracted with ethyl acetate, the organic phases were combined, and the combined organic phases were dried with anhydrous magnesium sulfate. The desiccant was filtrated by suction filtration, and the filtrate was evaporated to remove solvent with a rotary evaporator. The residue was purified by silica gel column chromatography (petroleum ether:ethyl acetate=30:1) to obtain 340 mg of white solid Ic with a yield of 39%.

Data for Ic:

White solid, melting point 102-104° C., $[\alpha]_D^{20}$ 117.6 (c, 0.5, CHCl$_3$).

| | |
|---|---|
| $^1$H NMR (400 MHz, CDCl$_3$) | δ 7.40 (d, J = 1.8 Hz, 2H), 7.32-7.26 (m, 2H), 7.23 (t, J = 7.5 Hz, 1H), 7.15-7.03 (m, 10H), 6.94 (dd, J = 7.8. 1.7 Hz, 2H), 6.86 (dd, J = 7.7, 1.7 Hz, 2H), 6.80 (dd, J = 6.6, 4.0 Hz, 1H), 6.66 (d, J = 7.3 Hz, 1H), 6.08 (d, J = 7.9 Hz, 1H), 4.20 (dd, J = 16.3, 4.3 Hz, 1H), 4.06 (dd, J = 16.3, 5.3 Hz, 1H), 3.82 (t, J = 5.5 Hz, 1H), 3.17-2.86 (m, 3H), 2.75 (dd, J = 15.7, 9.0 Hz, 1H), 2.48 (dd, J = 21.2, 11.3 Hz, 1H), 2.16-2.00 (m, 3H), 1.27 (s, 36H), 1.22 (s, 18H), 1.17 (s, 18H). |
| $^{13}$C NMR (101 MHz, CDCl$_3$) | δ 152.23 (d, J = 24.3 Hz), 150.50-150.30 (m), 149.83 (dd, J = 6.2, 4.2 Hz), 144.34 (d, J = 3.5 Hz), 144.13 (d, J = 2.5 Hz), 143.95 (d, J = 7.0 Hz), 143.56 (d, J = 22.2 Hz), 137.80 (d, J = 11.9 Hz), 136.36 (d, J = 13.1 Hz), 135.94 (s), 135.82 (d, J = 3.8 Hz), 135.61 (d, J = 6.3 Hz), 135.42 (d, J = 11.8 Hz), 135.13 (s), 133.37 (s), 133.16 (s), 131.81 (d, J =3.2 Hz), 128.54 (d, J = 23.5 Hz), 128.21 (s), 127.94 (dd, J = 20.0, 7.1 Hz), 126.88 (s), 126.29 (s), 125.96 (d, J = 5.3 Hz), 125.65 (s), 122.34 (d, J = 20.4 Hz), 121.70 (d, J = 31.3 Hz), 113.36 (s), 108.43 (s), 61.64 (d, J = 3.1 Hz), 45.51 (d, J = 26.4 Hz), 38.34 (d, J = 3.2 Hz), 36.23 (s), 34.77 (d, J = 9.9 Hz), 31.37 (t, J = 4.3 Hz), 30.93 (d, J = 36.6 Hz). |
| $^{31}$P NMR (162 MHz, CDCl$_3$) | δ −14.66, −17.59. |
| HR-MS (MALDI) | Calcd for C$_{80}$H$_{105}$NP$_2$ [M + H]$^+$: 1142.7795; Found: 1142.7798. |

Example 4

Synthetic Route of Ligand Id:

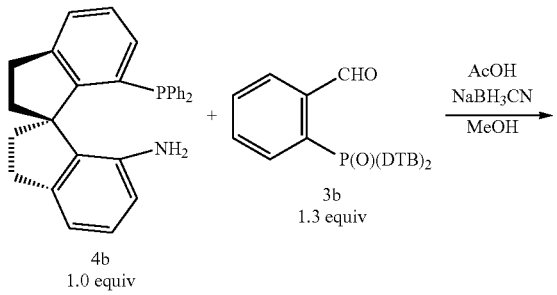

| | |
|---|---|
| ¹H NMR (400 MHz, CDCl₃) | δ 7.65 (s, 1H), 7.57 (s, 1H), 7.41 (d, J = 12.9 Hz, 2H), 7.33 (d, J = 12.8 Hz, 2H), 7.26 (s, 1H), 7.24 (s, 1H), 7.21 (d, J = 6.5 Hz, 4H), 7.13 (t, J = 7.5 Hz, 1H), 7.05-6.95 (m, 8H), 6.87 (dt, J = 14.8, 7.5 Hz, 2H) 6.73 (t, J = 7.7 Hz, 1H), 6.56 (d, J = 7.3 Hz, 1H), 5.40 (d, J = 7.9 Hz, 1H), 4.33 (dd, J = 18.3, 6.2 Hz, 1H), 4.19 (dd, J = 18.3, 4.4 Hz, 1H), 3.51 (t, J = 5.4 Hz, 1H), 3.15-2.76 (m, 4H), 2.40 (dd, J = 22.0, 10.8 Hz, 1H), 2.29-2.08 (m, 3H), 1.26 (d, J = 10.5 Hz, 36H). |
| ¹³C NMR (101 MHz, CDCl₃) | δ 152.23 (d, J = 24.9 Hz), 150.82 (dd, J = 21.3, 11.8 Hz), 144.76 (d, J = 7.5 Hz), 143.87 (d, J = 2.5 Hz), 143.72 (d, J = 7.4 Hz), 143.53 (d, J = 2.5 Hz), 138.33 (d, J = 13.8 Hz), 136.17 (d, J = 13.0 Hz), 134.02 (d, J = 22.4 Hz), 133.73 (s), 133.57 (s), 133.38 (s), 133.18 (s), 133.06 (s), 132.47 (s), 132.13 (s), 131.92 (d, J = 3.4 Hz), 131.81 (s), 131.28 (d, J = 33.7 Hz), 129.66 (s), 128.67 (s), 127.86 (d, J = 6.1 Hz), 127.78 (s), 127.72 (s), 127.33 (s), 126.80 (d, J = 9.6 Hz), 125.96 (dd, J = 10.4, 4.6 Hz), 125.78 (s), 125.53 (d, J = 12.3 Hz), 125.27 (d, J = 12.5 Hz), 113.10 (s), 107.66 (s), 61.32 (d, J = 3.3 Hz), 45.49 (d, J = 4.3 Hz), 38.80 (d, J = 4.8 Hz), 36.29 (s), 34.79 (d, J = 5.9 Hz), 31.12 (d, J = 5.2 Hz). |
| ³¹P NMR (162 MHz, CDCl₃) | δ 35.57, −20.90. |
| HR-MS (MALDI) | Calcd for $C_{64}H_{73}NOP_2$ [M + H]⁺: 934.5240; Found: 934.5245. |

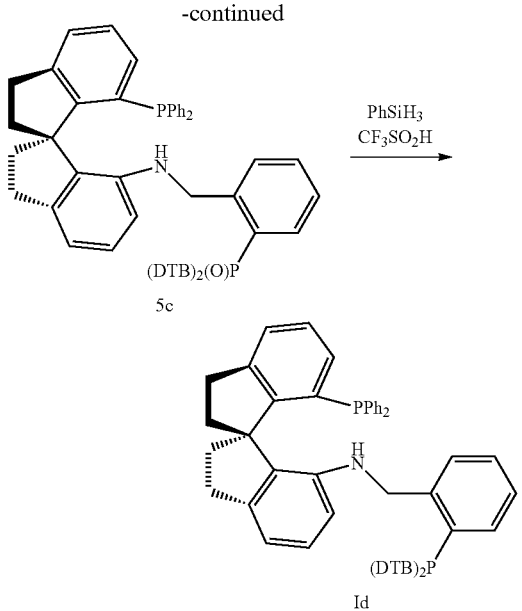

Synthesis of Intermediate 5c:

Under argon atmosphere, in to a 100 mL dry Schlenk tube was charged (R)-7'-(diphenylphosphino)-2,2',3,3'-tetrahydro-1,1'-spirobis[indene]-7-amine 4b (182 mg, 0.43 mmol). Was injected 20 mL of anhydrous methanol by the syringe. The mixture was stirred to dissolve. Was added 3b (300 mg, 0.57 mmol) and glacial acetic acid (33 μL, 0.57 mmol). The reaction mixture was stirred at 40° C. for 3 hours. Open the reverse plug, was added NaBH₃CN (165 mg, 2.58 mmol) in portion. The mixture was reacted at 40° C. for 12 hours. After the reaction was completed, it was cooled to room temperature, the system was spin-dried, and dichloromethane was added to dissolve, and the reaction solution was quenched with saturated sodium bicarbonate solution. The reaction solution was further extracted with dichloromethane, the combined organic phases were dried with anhydrous magnesium sulfate, the desiccant was filtrated by suction filtration, and the filtrate was evaporated to remove solvent with a rotary evaporator. The residue was purified by silica gel column chromatography (petroleum ether:ethyl acetate=3:1) to obtain a white solid 5c 399 mg with a yield of 98%.

Data of Intermediate 5c:

White solid, melting point 128-130° C., $[\alpha]_D^{20}$ 102.0 (c, 0.5, CHCl₃).

Synthesis of Ligand Id:

In to a 100 mL sealed tube was charged 5c (452 mg, 0.48 mmol), the tube air was replaced with argon, was added toluene (20 mL) and phenylsilane (239 μL, 1.94 mmol), at room temperature was added CF₃SO₂H (6.4 μL) dropwise to the reaction system. After dripping, the reaction was heated in an oil bath at 120° C. for 24 hours. Upon completion of the reaction, the reaction was quenched with trimethylamine and was extracted with ethyl acetate, the organic phases were combined, the combined organic phases were dried with anhydrous magnesium sulfate, the desiccant was filtrated by suction filtration, and the filtrate was evaporated with a rotary evaporator. The residue was purified by silica gel column chromatography (petroleum ether:ethyl acetate=30:1) to obtain 228 mg of white solid Id with a yield of 51%.

Data of Ligand Id:

White solid, melting point 108-110° C. $[\alpha]_D^{20}$ 114.0 (c, 0.5, CHCl₃).

| | |
|---|---|
| ¹H NMR (400 MHz, CDCl₃) | δ 7.53 (s, 1H), 7.48 (s, 1H), 7.34 (d, J = 7.4 Hz, 1H), 7.25 (d, J = 3.5 Hz, 2H), 7.23-7.00 (m, 16H), 7.00-6.88 (m, 2H), 6.86-6.78 (m, 1H), 6.71 (d, J = 7.3 Hz, 1H), 5.77 (d, J = 8.0 Hz, 1H), 3.97 (dd, J = 17.0, 5.1 Hz, 1H), 3.87 (dd, J = 16.9, 4.2 Hz, 1H), 3.54 (t, J = 5.4 Hz, 1H), 3.23-3.01 (m, 4H), 2.70-2.48 (m, 2H), 2.39 (td, J = 11.6, 5.7 Hz, 1H), 2.26 (dd, J = 12.7, 7.2 Hz, 1H), 1.33 (d, J = 12.6 Hz, 36H). |
| ¹³C NMR (101 MHz, CDCl₃) | δ 153.07 (d, J = 24.9 Hz), 150.68 (d, J = 6.8 Hz), 150.53 (d, J = 6.8 Hz), 144.12 (s), 144.09 (s), 144.02 (s), 143.58 (d, J = 2.2 Hz), 143.12 (d, J = 21.1 Hz), 139.33 (d, J = 13.7 Hz), 135.84 (d, J = 13.0 Hz), 135.35 (s), 135.26 (s), 135.10 (d, J = 2.2 Hz), 135.00 (s), 134.42-134.21 (m, 134.06 (s), 133.84 (d, J = 21.3 Hz), 133.11 (d, J = 19.0 Hz), 132.60 (s), 132.56 (s), 128.43 (d, J = 10.3 Hz), 128.26 (s), 128.16 (d, J = 1.8 Hz), 128.00 (s), 127.94 (s), 127.88 (s), 127.78 (d, J = 4.9 Hz), 127.52 (d, J = 14.8 Hz), 126.29 (s), 125.93 (s), 125.51 (d, J = 5.0 Hz), 122.47 (d, J = 9.6 Hz), 113.33 (s), 108.31 (s), 61.56 (d, J = 3.3 Hz), 45.23 (d, J = 27.3 Hz), 39.49 (d, J = 5.7 Hz), 36.31 (s), 34.84 (d, J = 4.7 Hz), 31.37 (d, J = 4.7 Hz), 30.91 (s). |
| ³¹P NMR (162 MHz, CDCl₃) | δ −13.71, −22.22. |
| HR-MS (MALDI) | Calcd for $C_{64}H_{73}NP_2$ $[M + H]^+$: 918.5291; Found: 918.5295. |

Example 5

Synthetic Route of Ligand Ie:

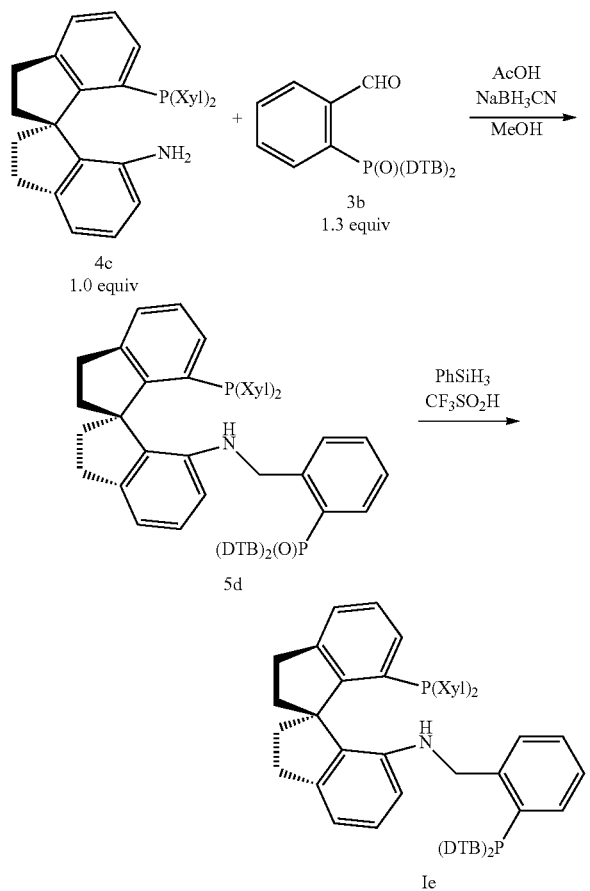

Synthesis of Intermediate 5d:

Under argon atmosphere, into a 100 mL dry Schlenk tube, was added (R)-7-(bis(3,5-dimethylphenyl)phosphino)-2,2,3,3'-tetrahydro-1,1'-spiro bis[indene]-7-amine 4c (300 mg, 0.63 mmol), 30 mL of anhydrous methanol was injected by the syringe, and the mixture was stirred to dissolve. Was added 3b (435 mg, 0.82 mmol) and glacial acetic acid (47 μL, 0.82 mmol). The reaction mixture was stirred at 40° C. for 3 hours. Open the reverse plug, was added NaBH₃CN (239 mg, 3.78 mmol) in portion, and the mixture was reacted at 40° C. for 12 hours. After completion of the reaction, the reaction mixture was cooled to room temperature, and the system was spin-dried, and was added dichloromethane to dissolve. The reaction mixture was quenched with saturated sodium bicarbonate solution and was extracted with dichloromethane. The organic phases were combined and dried with anhydrous magnesium sulfate. The desiccant was filtrated by suction, and the filtrate was evaporated to remove solvent with a rotary evaporator. The residue is purified by chromatographed on a silica gel column. (petroleum ether:ethyl acetate=3:1) affording 5d 545 mg of white solid with a yield of 87%.

Data for Intermediate 5d:

White solid, melting point 124-126° C., $[\alpha]_D^{20}$ 139.6 (c, 0.5, CHCl₃).

| | |
|---|---|
| ¹H NMR (400 MHz, CDCl₃) | δ 7.64 (s, 1H), 7.56 (s, 1H), 7.40 (s, 1H), 7.37 (s, 1H), 7.33 (s, 1H), 7.30 (s, 1H), 7.26 (s, 1H), 7.24-7.11 (m, 3H), 7.11-7.00 (m, 2H), 6.87 (ddd, J = 21.4, 14.7, 7.6 Hz, 3H), 6.69 (d, J = 7.5 Hz, 2H), 6.59 (t, J = 6.3 Hz, 4H), 5.55 (d, J = 7.9 Hz, 1H), 4.34 (dd, J = 18.0, 4.8 Hz, 1H), 4.14 (dd, J = 17.8, 5.7 Hz, 1H), 3.47 (t, 7 = 5.4 Hz, 1H), 3.07-2.74 (m, 4H), 2.36 (dd, J = 22.0, 10.5 Hz, 1H), 2.19 (s, 6H), 2.15-2.07 (m, 3H), 2.05 (s, 6H), 1.26 (d, J = 15.0 Hz, 36H). |
| ¹³C NMR (101 MHz, CDCl₃) | δ 151.95 (d, J = 24.3 Hz), 150.83 (dd, J = 11.2, 7.4 Hz), 144.76 (d, J = 7.1 Hz), 144.08 (d, J = 19.3 Hz), 143.66 (d, J = 7.0 Hz), 137.87 (d, J = 12.6 Hz), 137.09 (d, |

| | |
|---|---|
| | J = 6.8 Hz), 136.89 (d, J = 6.9 Hz), 135.76 (d, 7 = 12.2 Hz), 135.11 (d, J = 22.9 Hz), 133.35 (d, J = 12.2 Hz), 133.19 (s), 132.64 (s), 132.21 (s), 132.02 (s), 131.74 (s), 131.56 (s), 131.37 (s), 131.19 (s), 129.70 (d, J = 14.8 Hz), 129.51 (s), 128.52 (s), 127.63 (s), 127.19 (s), 127.06 (d, J = 9.6 Hz), 126.14 (s), 125.99 (d, J = 8.6 Hz), 125.82 (d, J = 3.8 Hz), 125.59 (d, J = 7.4 Hz), 125.27 (d, J = 12.3 Hz), 113.04 (s), 107.73 (s), 61.43 (s), 45.04 (s), 38.47 (s), 36.48 (s), 34.87 (d, J = 7.2 Hz), 31.19 (d, J = 6.1 Hz), 30.67 (s), 21.16 (s). |
| $^{31}$P NMR (162 MHz, CDCl$_3$) | δ 35.62, −20.12. |
| HR-MS (MALDI) | Calcd for C$_{68}$H$_{81}$NOP$_2$ [M + H]$^+$: 990.5866; Found: 990.5868. |

Synthesis of Ligand Ie:

Into a 100 mL sealed tube, was charged 5d (376 mg, 0.38 mmol), the tube air was replaced with argon, was added toluene (20 mL) and phenylsilane (188 μL, 1.52 mmol). CF$_3$SO$_2$H (5.1 μL) was added dropwise to the reaction system at room temperature, After dripping, the reaction mixture was heated in an oil bath at 120° C. for 24 hours. Upon completion of the reaction, the reaction mixture was quenched with trimethylamine and extracted with ethyl acetate. The organic phases were combined and were dried with anhydrous magnesium sulfate, the desiccant was filtrated by suction filtration, and the filtrate was evaporated to remove the solvent with a rotary evaporator. The residue was purified by silica gel column chromatography (petroleum ether:ethyl acetate=30:1) to obtain 145 mg of white solid Id with a yield of 39%.

Data for Ie:

White solid, melting point 115-117° C., [α]$_D^{20}$ 187.2 (c, 0.5, CHCl$_3$).

| | |
|---|---|
| $^1$H NMR (400 MHz, CDCl$_3$) | δ 7.40 (s, 1H), 7.34 (s, 1H), 7.17 (t, J = 7.4 Hz, 1H), 7.13-6.85 (m, 10H), 6.82 (s, 1H), 6.68 (dd, J = 12.9, 7.1 Hz, 2H), 6.61 (d, J = 8.5 Hz, 5H), 5.70 (d, J = 7.9 Hz, 1H), 3.86-3.69 (m, 2H), 3.36 (t, J = 5.3 Hz, 1H), 3.11-2.90 (m, 4H), 2.47 (td, J = 20.3, 10.7 Hz, 2H), 2.35-2.21 (m, 1H), 2.20-2.09 (m, 7H), 2.04 (s, 6H), 1.24 (s, 18H), 1.20 (s, 18H). |
| $^{13}$C NMR (101 MHz, CDCl$_3$) | δ 152.87 (d, J = 24.8 Hz), 150.50 (dd, J = 10.2, 6.6 Hz), 144.20 (d, J = 2.2 Hz), 143.89 (d, J = 7.7 Hz), 143.79 (s), 143.38 (d, J = 21.8 Hz), 139.12 (d, J = 13.0 Hz), 137.15 (d, J = 5.9 Hz), 136.99 (d, J = 8.0 Hz), 135.76 (d, J = 9.3 Hz), 135.34 (d, J = 3.4 Hz), 135.27 (s), 135.21 (s), 135.07 (d, J = 6.6 Hz), 134.95 (s), 134.11 (s), 132.90 (s), 132.80 (d, J = 3.0 Hz), 132.10 (d, J = 22.0 Hz), 130.83 (d, J = 19.2 Hz), 130.41 (s), 129.37 (s), 128.59 (s), 128.07 (d, J = 19.9 Hz), 127.81 (d, J = 5.3 Hz), 127.48 (d, J = 33.4 Hz), 126.24 (s), 125.71 (s), 125.51 (d, J = 4.8 Hz), 122.41 (d, J = 19.0 Hz), 113.30 (s), 108.37 (s), 61.65 (d, J = 2.8 Hz), 44.79 (d, J = 27.8 Hz), 39.41 (d, J = 5.4 Hz), 36.28 (s), 34.83 (d, J = 5.2 Hz), 31.37 (d, J = 5.7 Hz), 30.90 (s), 21.27 (s), |
| $^{31}$P NMR (162 MHz, CDCl$_3$) | δ −14.57, −22.31. |
| HR-MS (MALDI) | Calcd for C$_{68}$H$_{81}$NP$_2$ [M + H]$^+$: 974.5917; Found: 974.5922. |

Example 6

Synthetic Route of Ligand Ij:

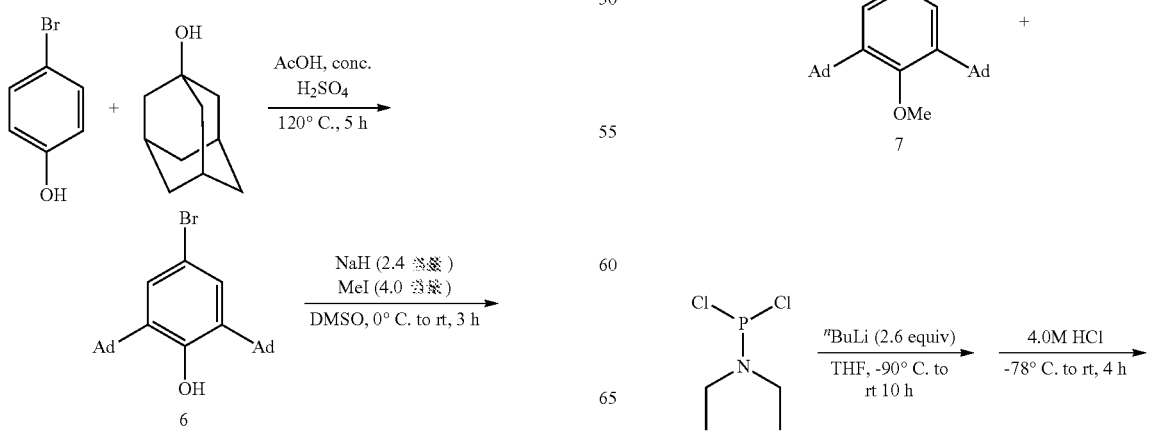

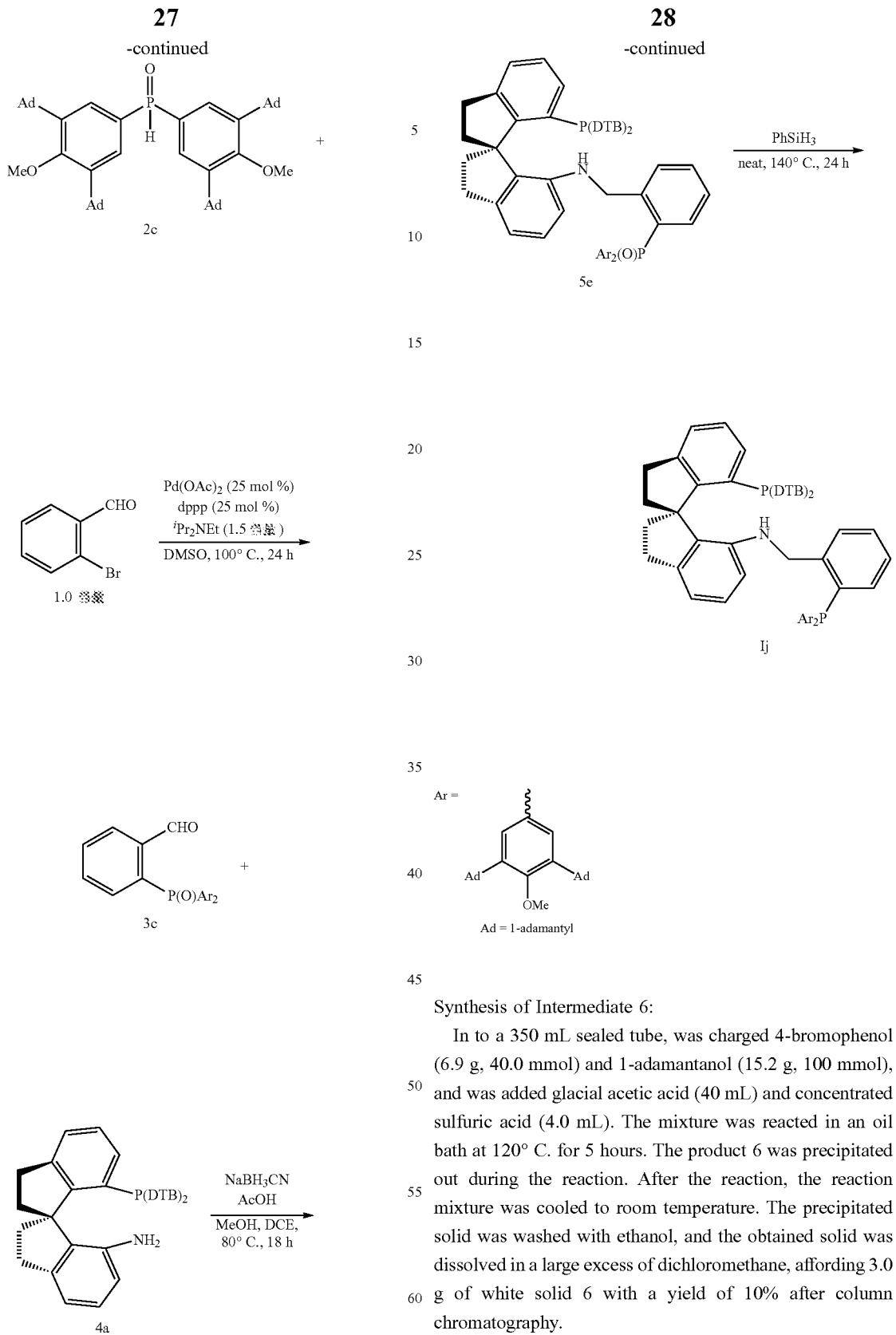

Synthesis of Intermediate 6:

In to a 350 mL sealed tube, was charged 4-bromophenol (6.9 g, 40.0 mmol) and 1-adamantanol (15.2 g, 100 mmol), and was added glacial acetic acid (40 mL) and concentrated sulfuric acid (4.0 mL). The mixture was reacted in an oil bath at 120° C. for 5 hours. The product 6 was precipitated out during the reaction. After the reaction, the reaction mixture was cooled to room temperature. The precipitated solid was washed with ethanol, and the obtained solid was dissolved in a large excess of dichloromethane, affording 3.0 g of white solid 6 with a yield of 10% after column chromatography.

Data for Intermediate 6:

$^1$H NMR (400 MHz, CDCl$_3$) δ 1.81 (m, 12 H), 2.13 (m, 18 H), 5.35 (s, 1 H), 7.23 (s, 2 H).

Synthesis of Intermediate 7:

In to a 100 mL dry three-necked flask, was added NaH (66 mg, 2.75 mmol) and anhydrous DMSO (5 mL). The temperature of the system was cooled to 0° C. by ice-water bath, and stirred vigorously to prevent DMSO from solidifying. Compound 6 (500 mg, 1.13 mmol) was dissolved in 40 mL DMSO, then the solution was added dropwise to the reaction system, and the mixture was stirred at 0° C. for 5 minutes after dropping. Methyl iodide (283 µL, 4.52 mmol) was added dropwise to the system, and the reaction was continued to stir for 15 minutes. The reaction temperature was then raised to room temperature and the reaction mixture was stirred for 2 hours. Upon completion of the reaction, the reaction mixture was quenched with ice water, and was extracted with dichloromethane, the organic phases were combined and dried over anhydrous magnesium sulfate, the desiccant was removed by suction filtration, and the filtrate was evaporated to remove the solvent with a rotary evaporator. The residue was subjected to silica gel column chromatography (petroleum ether) to obtain 446 mg of white solid 7 with a yield of 86%.

Data of Intermediate 7:

White solid, melting point 224-226° C.

| | |
|---|---|
| $^1$H NMR (400 MHz, CDCl$_3$) | δ 7.30 (s, 2H), 3.65 (s, 3H), 2.08 (s, 18H), 1.76 (s, 12H). |
| $^{13}$C NMR (101 MHz, CDCl$_3$) | δ 159.64, 146.00, 129.23, 116.81, 65.95, 42.50, 38.73, 36.78, 29.17. |
| HR-MS (EI) | Calcd for C$_{22}$H$_{35}$BrO [M]: 454.1871; Found: 454.1866. |

Synthesis of Intermediate 2c:

Under argon atmosphere, in to a 50 mL dry Schlenk tube was charged 7 (500 mg, 1.10 mmol), was injected 10 mL of anhydrous tetrahydrofuran by the syringe. The mixture was stirred to dissolve, the system temperature was cooled to −90° C. by an acetone liquid nitrogen bath. The n-butyl lithium solution (571 µL, 1.43 mmol) was added dropwise, and after dripping, the mixture was reacted with stirring for 2 hours. Diethyldichlorophosphine (80 µL, 0.55 mmol) was added dropwise to the reaction system, after dropping, the reaction was continued reacted with stirring at −90° C. for 2 hours, and then the mixture was naturally warmed to room temperature and stirred overnight. The temperature of the reaction system was cooled to −78° C., hydrochloric acid solution (4.0 mL, 4.0 M in dioxane) was added dropwise, and after dropping, the temperature was raised to room temperature and the reaction mixture was stirred for 4 hours. Upon completion of the reaction, water was added to quench the reaction. The reaction mixture was extracted with ethyl acetate, and the organic phases were combined, the combined organic phases were dried with anhydrous magnesium sulfate, the desiccant was filtrated to remove by suction filtration, and the filtrate was evaporated to remove the solvent with a rotary evaporator. The residue was purified by silica gel column chromatography (petroleum ether:ethyl acetate=3:1) to obtain 248 mg of white solid 2c with a yield of 56%.

Data for Intermediate 2c:

White solid, melting point >250° C.

| | |
|---|---|
| $^1$H NMR (400 MHz, CDCl$_3$) | δ 8.63 (s, 0.5H), 7.55 (s, 2H), 7.51 (s, 2H), 7.45 (s, 0.5H), 3.67 (s, 6H), 2.10-2.02 (m, 36H), 1.74 (s, 24H). |
| $^{13}$C NMR (101 MHz, CDCl$_3$) | δ 164.14 (d, J = 3.1 Hz), 144.57 (d, J = 12.7 Hz), 129.06 (d, J = 13.1 Hz), 124.75 (d, J = 105.1 Hz), 66.02 (s), 61.67 (s), 44.88 (s), 42.50 (s), 38.73 (s), 36.70 (s), 29.05 (s). |
| $^{31}$P NMR (162 MHz, CDCl$_3$) | δ 22.71. |
| HR-MS (MALDI) | Calcd for C$_{54}$H$_{71}$O$_3$P [M + H]$^+$: 799.5214; Found: 799.5218. |

Synthesis of intermediate 3c:

To a 50 mL sealed tube, Pd(OAc)$_2$ (24 mg), dppp (43 mg), 2c (395 mg), degassed DMSO (10 mL), 2-bromobenzaldehyde (48 µL) and $^i$Pr$_2$NEt (104 µL) were added sequentially. The mixture was stirred at 100° C. for 24 h. Upon completion, the reaction mixture was cooled to room temperature and diluted with EtOAc (20 mL) and H$_2$O (20 mL). The resulting mixture was extracted with EtOAc. The combined organic layers were dried over MgSO$_4$ and the solvent was evaporated. The residue was purified by silica gel column chromatography (petroleum ether:ethyl acetate=5:1), affording 752 mg of white solid 3c with 62% yield.

Data for Intermediate 3c:
White-solid, melting-point 198-200° C.

| | |
|---|---|
| $^1$H NMR (400 MHz, CDCl$_3$) | δ 10.81 (s, 1H), 8.16 (d, J = 7.2 Hz, 1H), 7.68 (t, J = 7.3 Hz, 1H), 7.59 (t, J = 7.4 Hz, 1H), 7.43 (d, J = 13.0 Hz, 4H), 7.30-7.24 (m, 1H), 3.69 (s, 6H), 2.01 (s, 36H), 1.71 (s, 24H). |
| $^{13}$C NMR (101 MHz, CDCl$_3$) | δ 190.44 (d, J = 5.5 Hz), 162.76 (d, J = 3.3 Hz), 143.23 (d, J = 12.4 Hz), 138.20 (d, J = 6.5 Hz), 134.95 (d, J = 94.4 Hz), 132.31 (d, J = 10.7 Hz), 131.35 (d, J = 11.7 Hz), 130.76 (d, J = 1.6 Hz), 128.99 (d, J = 11.9 Hz), 127.25 (d, J = 8.7 Hz), 124.42 (d, J = 109.3 Hz), 64.80 (s), 41.21 (s), 37.49 (s), 35.44 (s), 27.81 (s). |
| $^{31}$P NMR (162 MHz, CDCl$_3$) | δ 33.33. |
| HR-MS (MALDI) | Calcd for C$_{61}$H$_{75}$O$_4$P [M + H]$^+$: 903.5476: Found: 903.5478. |

Synthesis of Intermediate 5e:

Under argon atmosphere, in to a 100 mL dry Schlenk tube, was charged (R)-7'-bis-(3,5-di-tert-butylphenyl)phosphino-7'-amino-1,1'-spiroindene 4a (199 mg, 0.31 mmol), and 15 mL of anhydrous methanol was injected by the syringe, and the mixture was stirred to dissolve. Was added 3c (420 mg, 0.47 mmol) and glacial acetic acid (70 µL, 1.24 mmol). The mixture was reacted with stirring at 80° C. for 5 hours. Open the reverse plug, was added NaBH$_3$CN (117 mg, 1.86 mmol) in portion, the mixture was reacted at 80° C. for 13 hours. After the reaction was completed, it was cooled to room temperature, the system was spin-dried, and dichloromethane was added to dissolve, and the reaction mixture was quenched with saturated sodium bicarbonate solution. The reaction mixture was extracted with dichloromethane. The organic phases were combined and dried with anhydrous magnesium sulfate. The desiccant was removed by suction filtration, and the filtrate was evaporated to remove the solvent with a rotary evaporator. The residue was purified by silica gel column chromatography (petroleum ether:ethyl acetate=3:1) to obtain 465 mg of white solid 5e with a yield of 98%.

Data for Intermediate 5e:
White solid, melting-point 205-207° C., [α]$_D^{20}$ 99.2 (c, 0.5, CHCl$_3$).

| | |
|---|---|
| $^1$H NMR (400 MHz, CDCl$_3$) | δ 7.44-7.38 (m, 5H), 7.27-6.87 (m, 11H), 6.78 (d, J = 6.9 Hz, 2H), 6.54 (d, J = 7.3 Hz, 1H), 5.79 (d, 7 = 7.9 Hz, 1H), 4.89 (dd, J = 17.5, 5.5 Hz, 1H), 4.29 (dd, J = 17.3, 4.5 Hz, 1H), 3.85 (t, J = 5.3 Hz, 1H), 3.67 (d, J = 9.5 Hz, 6H), 3.04-2.84 (m, 2H), 2.81-2.63 (m, 1H), 2.35 (dt, J = 30.7, 10.4 Hz, 2H), 2.02 1.98 (m, 36H), 1.93-1.76 (m, 3H), 1.70 (d, J = 8.5 Hz, 24H), 1.20 (s, 18H), 1.08 (s, 18H), |
| $^{13}$C NMR (101 MHz, CDCl$_3$) | δ 163.69 (d, J = 2.1 Hz), 163.57 (d, J = 2.9 Hz), 151.31 (d, J = 23.7 Hz), 150.09 (d, J = 7.5 Hz), 149.71 (d, J = 5.0 Hz), 145.13 (d, J = 4.0 Hz), 144.83 (d, J = 7.6 Hz), 144.26 (s), 144.10 (d, J = 8.3 Hz), 143.93 (s), 143.85 (s), 137.34 (d, J = 14.2 Hz), 136.55 (d, J = 11.2 Hz), 135.53 (d, J = 24.5 Hz), 133.44 (d, J = 11.9 Hz), 132.33 (d, J = 31.3 Hz), 130.75 (s), 130.55 (d, J = 11.6 Hz), 130.40 (s), 130.14 (d, J = 11.6 Hz), 129.50 (d, J = 22.2 Hz), 128.13 (s), 127.59 (d, J = 18.5 Hz), 127.29 (dd, J = 9.2, 5.3 Hz), 127.06 (d, J = 9.7 Hz), 126.92 (s), 125.99 (d, J = 8.7 Hz), 125.61 (s), 125.49 (d, J = 12.7 Hz), 122.30 (s), 121.24 (s), 113.38 (s), 107.92 (s), 66.04 (d, 7 = 5.5 Hz), 61.60 (d, 7 = 2.4 Hz), 46.05 (d, J = 3.9 Hz), 42.61 (d, J = 3.5 Hz), 38.78 (s), 36.85 (s), 34.75 (d, J = 7.7 Hz), 31.38 (s), 29.21 (s). |
| $^{31}$P NMR (162 MHz, CDCl$_3$) | δ 34,46. −13.68. |
| HR-MS (MALDI) | Calcd for C$_{106}$H$_{133}$NO$_3$P$_2$ [M + H]$^+$: 1530.9833; Found: 1530.9835. |

Synthesis of Ligand Ij:

Into a 25 mL sealed tube was charged 5e (460 mg, 0.40 mmol). The air was replaced with argon gas, and phenylsilane (4.0 mL) was added. The mixture was heated by oil bath at 140° C. for reacting 24 hours. Upon completion of the reaction, the solvent in the system was removed by a rotary evaporator. The residue was purified by silica gel column chromatography (petroleum ether:ethyl acetate=30:1) to obtain 386 mg of white solid Ij with a yield of 85%.

Data for Ligand Ij:

White solid, melting point 193-195° C., $[\alpha]_D^{20}$ 88.4 (c, 0.5, $CHCl_3$).

| | |
|---|---|
| $^1$H NMR (400 MHz, $CDCl_3$) | δ 7.25 (s, 3H), 7.17 (t, J = 7.4 Hz, 1H), 7.05 (t, J = 8.9 Hz, 4H), 7.01-6.94 (m, 5H), 6.87 (d, J = 7.7 Hz, 2H), 6.83 (d, J = 7.8 Hz, 2H), 6.72-6,64 (m, 1H), 6.60 (d, J = 7.4 Hz, 1H), 5.99 (d, J = 7.9 Hz, 1H), 4.20 (dd, J = 16.7, 5.2 Hz, 1H), 4.07 (dd, J = 16.3, 5.2 Hz, 1H), 3.80 (t, J = 5.4 Hz, 1H), 3.66 (s, 6H), 3.11-2.92 (m, 2H), 2.92-2.77 (m, 1H), 2.66 (dd, J = 15.6, 9.3 Hz, 1H), 2.43 (dd, J = 21.8, 10.9 Hz, 1H), 2.12-2.04 (m, 2H), 1.99 (s, 36H), 1.93-1.85 (m, 1H), 1.70 (s, 24H), 1.17 (s, 18H), 1.13 (s, 18H), |
| $^{13}$C NMR (101 MHz, $CDCl_3$) | δ 159.88 (d, J = 24.7 Hz), 151.03 (d, J = 24.3 Hz), 148.83 (dd, J = 11.0, 6.4 Hz), 143.47 (d, J = 3.7 Hz), 143.14 (d, J = 2.2 Hz), 142.91 (d, J = 7.0 Hz), 142.51-142.31 (m), 142.17 (s), 136.42 (d, J = 11.8 Hz), 135.59 (s), 135.44 (d, J = 3.6 Hz), 135.26 (s), 134.34 (d, J = 23.7 Hz), 132.23 (s), 131.79 (s), 131.02 (d, J = 10.9 Hz), 130.82 (d, J = 10.6 Hz), 130.59 (d, J = 3.2 Hz), 129.15 (d, J = 8.3 Hz), 128.90 (d, J = 7.7 Hz), 127.54 (d, J = 7.6 Hz), 127.29 (d, J = 15.7 Hz), 126.86 (d, J = 20.3 Hz), 125.86 (s), 125.27 (s), 124.82 (d, J = 5.3 Hz), 124.59 (s),120.69 (d, J = 5.2 Hz), 112.33 (s), 107.29 (s), 64.74 (d, J = 3.1 Hz), 60.62 (d, J = 3.3 Hz), 44.45 (d, J = 26.3 Hz), 41.66 (s), 37.59 (s), 35.91 (s), 33.71 (d, J = 2.4 Hz), 30.37 (d, J = 12.7 Hz), 28.24 (s). |
| $^{31}$P NMR (162 MHz, $CDCl_3$) | δ -16.46, -17.32. |
| HR-MS (MALDI) | Calcd for $C_{106}H_{133}NO_2P_2$ $[M + H]^+$: 1514.9884; Found: 1514.9886. |

DESCRIPTION OF THE DRAWINGS

FIG. 1 is a schematic diagram of the structure of the catalyst IIf in the present invention.

Example 7

Synthetic Route of Catalyst IIf:

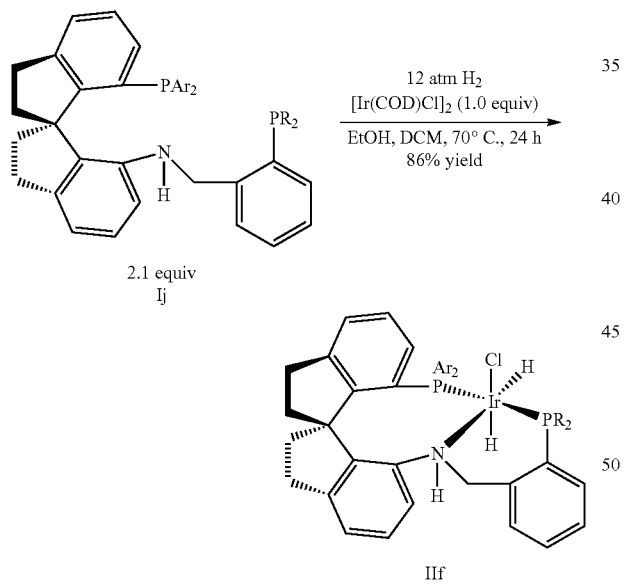

In the glove box, was added the catalyst precursor [Ir(COD)Cl]$_2$ (31 mg) and the ligand Ij (150 mg) into a 25 mL schlenk tube, and was added ethanol (5 mL) and dichloromethane (2 mL). The mixed solution was transferred to a hydrogenation kettle, which was filled with 12 atm hydrogen, and the mixture was reacted in an oil bath at 70° C. for 24 hours. Upon completion of the reaction, the reaction was cooled to room temperature. Then hydrogen was slowly released, and the solvent was removed from the system with a rotary evaporator. The residue was purified by silica gel column chromatography (petroleum ether:ethyl acetate=10:1) to obtain 142 mg of white solid IIf with a yield of 86%.

Data for Catalyst IIf:

| | |
|---|---|
| $^1$H NMR (400 MHz, $CDCl_3$) | δ 7.49-7.31 (m, 8H), 7.26-7.24 (m, 2H), 7.22-7.00 (m, 7H), 6.51 (t, J = 7.7 Hz, 1H), 6.16 (d, J = 7.2 Hz, 1H), 5.75 (d, J = 8.2 Hz, 1H), 5.38 (s, 1H), 4.87 (d, J = 10.2 Hz, 1H), 4.27 (d, J = 12.1 Hz, 1H), 3.64 (s, 3H), 3.58 (s, 3H), 3.18-2.96 (m. 1H), 2.92 (dd, J = 16.1, 8.1 Hz, 1H), 2.55-2.39 (m, 1H), 2.15 (dd, J = 12.0, 6.8 Hz, 1H), 2.09-1.58 (m, 64H), 1.21 (d, J = 51.4 Hz, 36H), -22.22 (ddd, J = 17.0, 13.5, 8.3 Hz, 1H), -23.68--23.90 (m, 1H). |
| $^{31}$P NMR (162 MHz, $CDCl_3$) | δ 24.28 (dd, J = 366.0, 12.6 Hz), 12.40 (dd, J = 366.0, 16.7 Hz). |
| HR-MS (ESI) | Calcd for $C_{106}H_{135}IrNO_2P_2$ $[M - Cl]^+$: 1708.9592; Found: 1708.9582 |

Single crystal: see the attached drawings in the specification.

Single Crystal Data of Catalyst IIf:

| Empirical formula | $C_{106}H_{135}ClIrNO_2P_2$ |
|---|---|
| Formula weight | 1744.73 |
| Temperature | 294.15 K |
| Crystal system | monoclinic |
| Space group | $P2_1$ |
| a/Å | 11.29730(3) |
| b/Å | 23.03721(6) |
| c/Å | 19.69944(5) |
| α/° | 90 |
| β/° | 93.1830(2) |
| γ/° | 90 |
| Volume/Å$^3$ | 5119.03(2) |
| Z | 2 |
| $p_{calc}$g/cm$^3$ | 1.132 |
| μ/mm$^{-1}$ | 3.391 |
| F(000) | 1836.0 |
| Crystal size/mm$^3$ | 0.34 × 0.24 × 0.22 |
| Radiation | CuKα (λ = 1.54184) |
| 2Θ range for data collection/° | 7.676 to 159.104 |
| Index ranges | −14 ≤ h ≤ 14, −24 ≤ k ≤ 29, −24 ≤ l ≤ 25 |
| Reflections collected | 703 82 |
| Independent reflections | 19990 [$R_{int}$ = 0.0231, $R_{sigma}$ = 0.0203] |
| Data/restraints/parameters | 19990/160/1128 |
| Goodness-of-fit on F$^2$ | 1.035 |
| Final R indices [I > 2σ(I)] | $R_1$ = 0.0273, w$R_2$ = 0.0741 |
| Final R indices (all data) | $R_1$ = 0.0275, w$R_2$ = 0.0742 |
| Largest diff. peak/hole e Å$^{-3}$ | 0.72/−0.55 |
| Flack parameter | −0.027(4) |

Example 8

The application of chiral spirocyclic phosphine-nitrogen-phosphine tridentate ligand iridium complex in the asymmetric catalytic hydrogenation of carbonyl compounds.

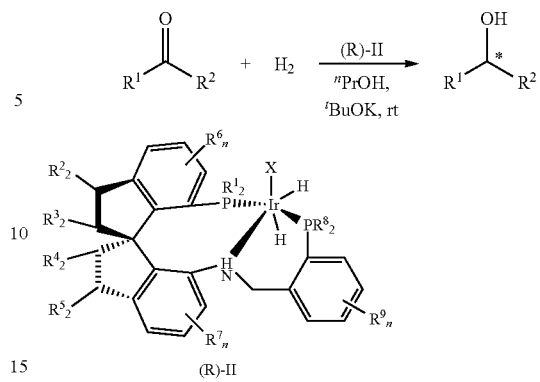

(R)-II

Was charged the catalyst (R)-II in the glove box, potassium tert-butoxide was added into the hydrogenation inner tube, was added the solvent n-propanol and hydrogenation substrate. The hydrogenation inner tube was put into the hydrogenation kettle, and quickly replacing the gas of the reaction kettle with hydrogen by three times, and finally adjusting the hydrogen pressure to 8-12 atm. Stirring the reaction at room temperature until the hydrogen pressure no longer decreased. The hydrogen in the reactor was slowly released, and the crude product was obtained after the solvent is removed by the rotary evaporator. After the catalyst was removed by filtration through a short silica gel column, the conversion rate and yield of the reaction were analyzed by thin layer chromatography and nuclear magnetic resonance, and the optical purity of the product was analyzed by high performance liquid chromatography. The obtained hydrogenation experiment results was shown in Table 1.

TABLE 1

Asymmetric catalytic hydrogenation of carbonyl compounds

| NO. | carbonyl compounds | II | S/C | Yield (%) | Ee (%) |
|---|---|---|---|---|---|
| 1 | $C_2H_5$ C(=O) CH$_3$ | (R)-IIf | 150 | 99 | 90 |
| 2 | $C_3H_7$ C(=O) CH$_3$ | (R)-IIf | 150 | 99 | 91 |
| 3 | $C_4H_9$ C(=O) CH$_3$ | (R)-IIf | 150 | 99 | 92 |
| 4 | $C_5H_{11}$ C(=O) CH$_3$ | (R)-IIr | 150 | 99 | 91 |
| 5 | $C_6H_{13}$ C(=O) CH$_3$ | (R)-IIf | 150 | 99 | 91 |
| 6 | $C_7H_{15}$ C(=O) CH$_3$ | (R)-IIf | 150 | 99 | 91 |

TABLE 1-continued

Asymmetric catalytic hydrogenation of carbonyl compounds

| NO. | carbonyl compounds | II | S/C | Yield (%) | Ee (%) |
|---|---|---|---|---|---|
| 7 | C₈H₁₇-C(O)-CH₃ | (R)-IIr | 150 | 99 | 90 |
| 8 | (CH₃)₂CH-C(O)-CH₃ | (R)-IIf | 150 | 99 | 99.8 |
| 9 | HO-(CH₂)₄-C(O)-CH₃ | (R)-IIf | 150 | 96 | 90 |
| 10 | CH₂=CH-CH₂-CH₂-C(O)-CH₃ | (R)-IIf | 150 | 99 | 92 |
| 11 | MeOOC-(CH₂)₃-C(O)-CH₃ | (R)-IIf | 150 | 99 | 90 |
| 12 | NC-(CH₂)₂-C(O)-CH₃ | (R)-IIf | 150 | 97 | 95 |
| 13 | pentoxifylline-like ketone | (R)-IIf | 150 | 99 | 86 |
| 14 | cycloheptyl methyl ketone | (R)-IIf | 150 | 99 | 99.2 |
| 15 | cyclohexyl methyl ketone | (R)-IIf | 150 | 99 | 99.5 |
| 16 | 1-acetyl-4-acetylpiperidine | (R)-IIr | 150 | 99 | 99.2 |
| 17 | 4-acetyltetrahydropyran | (R)-IIf | 150 | 99 | 99.3 |

TABLE 1-continued
Asymmetric catalytic hydrogenation of carbonyl compounds
| NO. | carbonyl compounds | II | S/C | Yield (%) | Ee (%) |
|---|---|---|---|---|---|
| 18 | 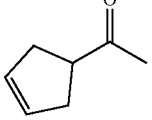 | (R)-IIf | 150 | 99 | 98 |
| 19 | 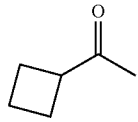 | (R)-IIf | 150 | 98 | 95 |
| 20 | 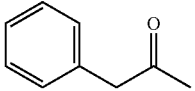 | (R)-IIr | 150 | 98 | 91 |
| 21 | 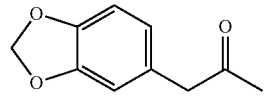 | (R)-IIf | 150 | 99 | 92 |
| 22 | 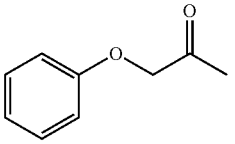 | (R)-IIf | 150 | 99 | 87 |
| 23 | 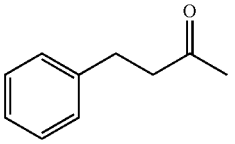 | (R)-IIr | 5000 | 85 | 95 |
| 24 | 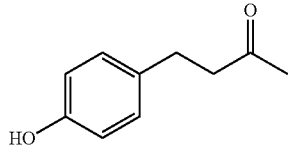 | (R)-IIf | 150 | 99 | 95 |
| 25 | 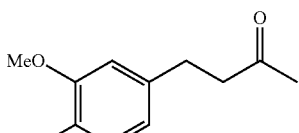 | (R)-IIf | 150 | 99 | 94 |
| 26 | 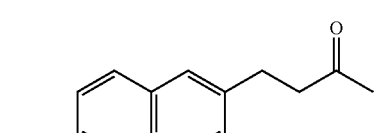 | (R)-IIf | 150 | 99 | 94 |
| 27 | 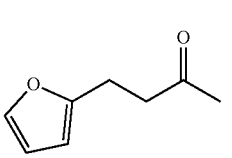 | (R)-IIr | 150 | 95 | 94 |

TABLE 1-continued

Asymmetric catalytic hydrogenation of carbonyl compounds

| NO. | carbonyl compounds | II | S/C | Yield (%) | Ee (%) |
|---|---|---|---|---|---|
| 28 | (1-methylindol-3-yl)propyl methyl ketone | (R)-IIf | 150 | 90 | 94 |
| 29 | 4-(thiophen-2-yl)butan-2-one | (R)-IIf | 150 | 99 | 91 |
| 30 | 3,3-dimethylcyclohexan-1-one | (R)-IIf | 150 | 95 | 92 |
| 31 | 2,2-dimethyltetrahydro-4H-pyran-4-one | (R)-IIr | 150 | 99 | 94 |
| 32 | N-Boc-piperidin-3-one | (R)-IIf | 150 | 99 | 90 |
| 33 | N-Cbz-piperidin-3-one | (R)-IIf | 150 | 90 | 82 |
| 34 | N-Boc-pyrrolidin-3-one | (R)-IIf | 150 | 68 | 94 |
| 35 | heptane-2,6-dione | (R)-IIf | 150 | 54 | 99.4 |
| 36 | octane-2,7-dione | (R)-IIf | 150 | 87 | 99.5 |
| 37 | 1,4-phenylenebis(propan-2-one) | (R)-IIf | 150 | 86 | 99.5 |

We claim:
1. A chiral spirocyclic phosphine-nitrogen-phosphine tridentate ligand SpiroPNP comprising a compound having a structure of general formula I, its optical isomer, a racemate thereof, or a salt thereof as shown below:

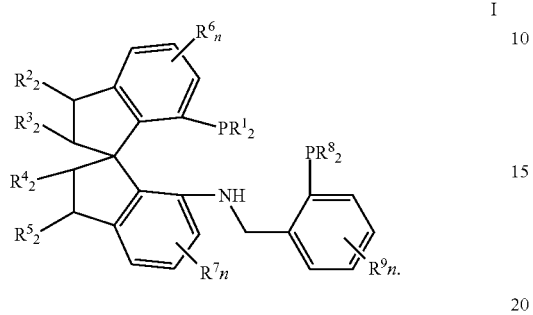

I wherein $R^1$ is selected from the group consisting of C1-C10 hydrocarbyl, phenyl, substituted phenyl, 1-naphthyl, 2-naphthyl, heteroaryl and benzyl, and the substituent on the phenyl group is C1-C10 hydrocarbyl, alkoxy, the number of substituents of the phenyl group is 1 to 5, and the heteroaryl is selected from the group consisting of furyl, thienyl and pyridyl;

$R^2$, $R^3$, $R^4$ and $R^5$ are independently selected from the group consisting of H, C1-C10 alkyl, phenyl, substituted phenyl, 1-naphthyl, 2-naphthyl, heteroaryl and benzyl, and the substituent on the phenyl group is C1-C10 hydrocarbyl or alkoxy, the number of substituents on the phenyl group of $R^2$, $R^3$, $R^4$, $R^5$ are 1 to 5, and the heteroaryl is selected independently from the group consisting of furyl, thienyl and pyridyl, and the $R^2$ and $R^3$, $R^4$ and $R^5$ are optionally formed into C3-C7 aliphatic ring or heteroaromatic ring, $R^6$ and $R^7$ are independently selected from the group consisting of H, C1-C10 alkyl, C1-C10 alkoxy and C1-C10 aliphatic amido group, and n=0~3, or when n≥2, two adjacent $R^6$ groups or two adjacent $R^7$ groups can be formed into $C_3$-$C_7$ aliphatic ring or heteroaromatic ring, $R^8$, $R^9$ are selected from the group consisting of H, $C_1$-$C_{10}$ alkyl, $C_1$-$C_{10}$ alkoxy, phenyl, substituted phenyl, 1-naphthyl, 2-naphthyl, heteroaryl benzyl, C2-C4 carbon chain and carbon chains containing nitrogen atom, oxygen atom or sulfur atom, and the substituent on the phenyl group is $C_1$-$C_{10}$ alkyl or alkoxy, the number of a substituents of the phenyl group of $R^8$, $R^9$ are 1 to 5, and said heteroaryl is selected independently from the group consisting of furyl, thienyl and pyridyl, and adjacent $R^8$ and $R^9$ groups can be formed into rings and $R^8$, $R^9$ can be the same or different.

2. The chiral spirocyclic phosphine-nitrogen-phosphine tridentate ligand according to claim 1, comprising the compound having the following structure formula its optical isomer racemate thereof, or the salt thereof as shown below:

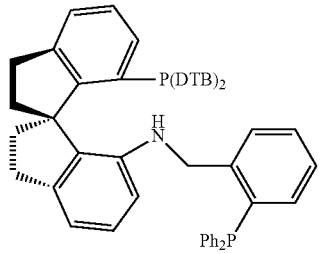

Ia

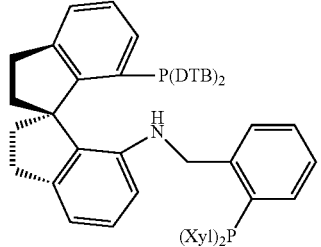

Ib

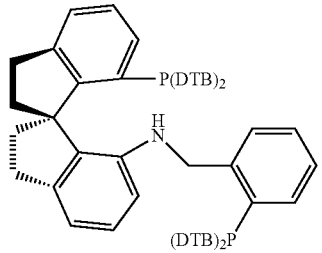

Ic

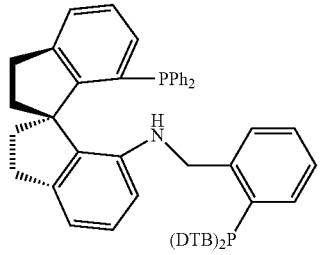

Id

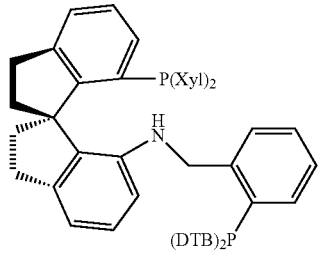

Ie

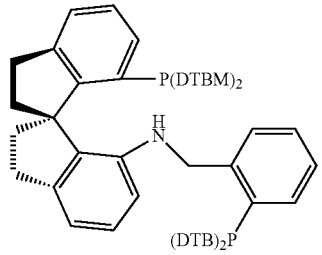

If

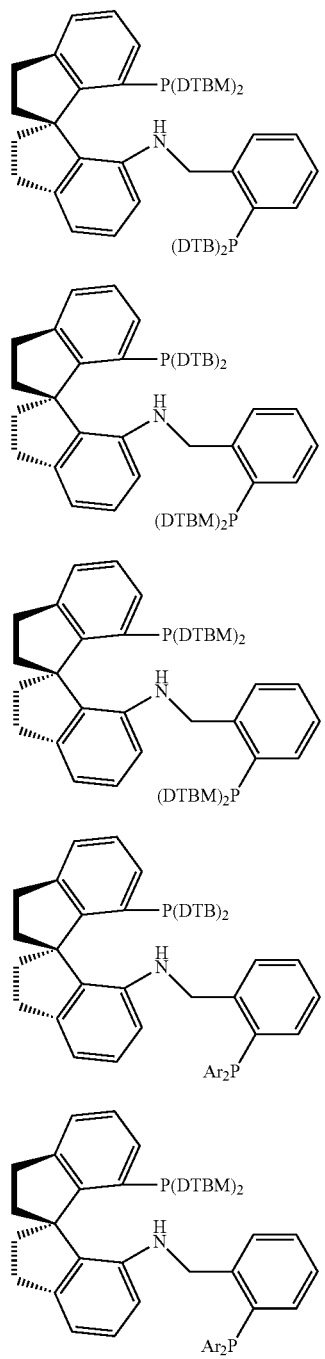

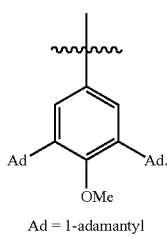

Ar =

Ad = 1-adamantyl

3. A method for synthesizing the chiral spirocyclic phosphine-nitrogen-phosphine tridentate ligand SpiroPNP having the structure formula I according to claim 1, comprising the following reaction steps:

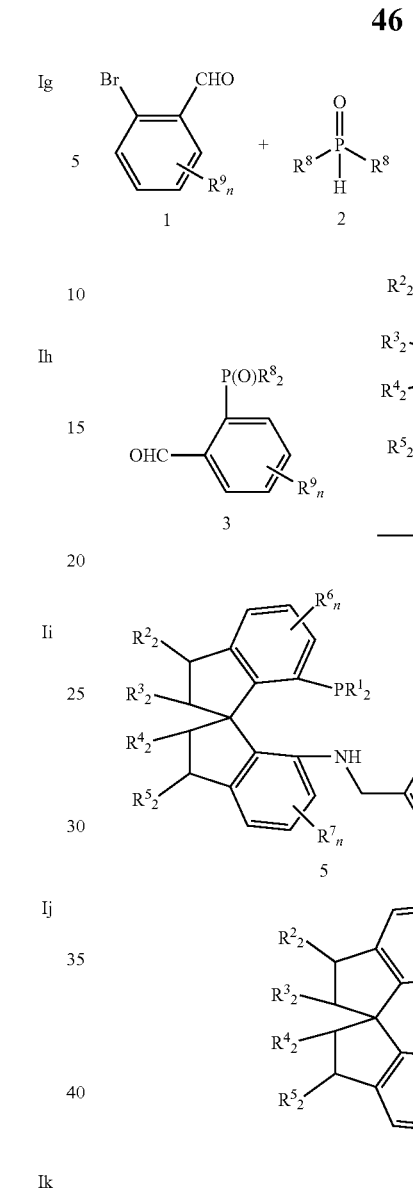

first reacting a compound represented by formula 1 with a compound represented by formula 2 in a reactor for 12 to 24 hours in the presence of an organic solvent, a base and a palladium catalyst, to obtain a compound represented by formula 3, the compound represented by formula 3 and a compound represented by formula 4 undergo reductive amination in the presence of a reducing agent to obtain a compound represented by formula 5;

the compound represented by formula 5 undergo a reductive reaction in the presence of an organic solvent and a reducing agent to form the chiral spirocyclic phosphine-nitrogen-phosphine tridentate ligand SpiroPNP having structure of formula I, wherein, $R^1$ to $R^9$ in formula 1, 2, 3, 4, 5, I, are defined as in claim 1.

4. The preparation method according to claim 3, wherein, the organic solvent is selected from the group consisting of a single or mixture solvents of methanol, ethanol, propanol, isopropanol, butanol, tetrahydrofuran, toluene, xylene, methyl tert-butyl ether, diethyl ether, dioxane, N,N-dimethylformamide, dimethyl sulfoxide, dichloromethane, chloroform or 1,2-dichloroethane; the reducing reagent is selected from the group consisting of lithium aluminum hydride, sodium borohydride, sodium triacetoxyborohydride, sodium nitrile borohydride, trichlorosilane and phenylsilane; said base maybe organic base or inorganic base, said organic base maybe pyridine, triethylamine, tributyl amine, N-methylmorpholine and N,N-diethylisopropylamine; said inorganic base maybe sodium hydroxide, potassium hydroxide, sodium carbonate and potassium carbonate; said palladium catalyst maybe palladium acetate and palladium on carbon; said iridium catalyst maybe 1,5-cyclooctadiene iridium chloride dimer and bis(1,5-cyclooctadiene)di-methoxydiiridium.

5. A method of using the chiral spirocyclic phosphine-nitrogen-phosphine tridentate ligand SpiroPNP having the structure of formula I according to claim 1, comprising the reaction steps:
adding a compound having a carbonyl functional group into a reaction mixture of the chiral spirocyclic phosphine-nitrogen-phosphine tridentate ligand having the structure of formula I, and an iridium salt precursor to performance an asymmetric catalytic hydrogenation reaction to obtain alcohol compound.

6. A chiral spirocyclic phosphine-nitrogen-phosphine tridentate iridium catalyst Ir-SpiroPNP comprising a compound having the structure of formula II, its optical isomer, a racemate thereof, or a salt thereof as shown below:

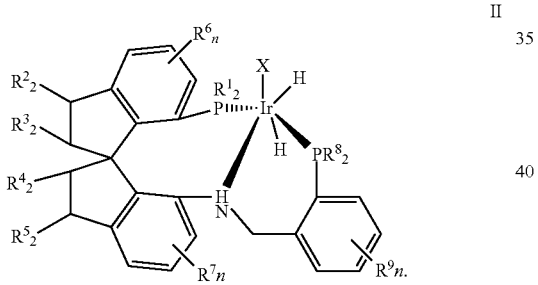

II wherein, the definition of R¹ to R⁹ in formula II is the same as in claim 1, X is Cl⁻, Br⁻, OMe⁻, BF₄⁻ or OTf⁻.

7. The chiral spirocyclic phosphine-nitrogen-phosphine tridentate iridium catalyst Ir-SpiroPNP according to claim 6, comprising the compound having the structure of the following formula its optical isomer racemate thereof, or the salt thereof as shown below:

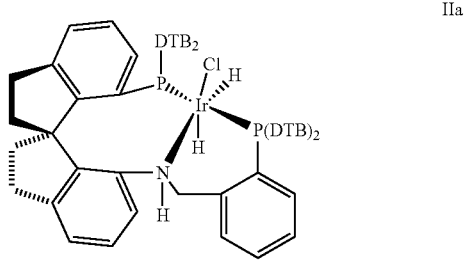

IIa

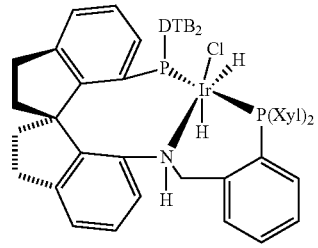

IIb

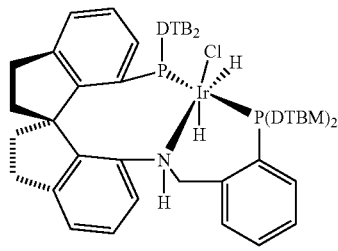

IIc

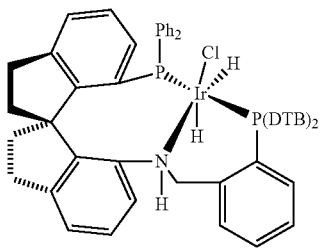

IId

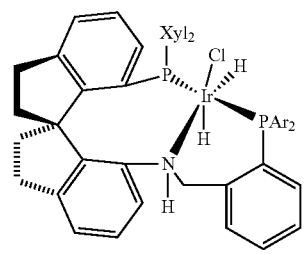

IIe

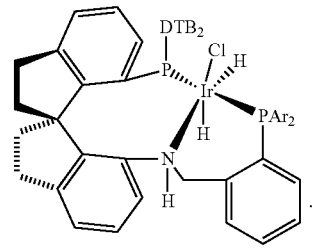

IIf

Ar = [3,5-(1-Ad)₂-4-MeOC₆H₂]

8. The chiral spirocyclic phosphine-nitrogen-phosphine tridentate iridium catalyst Ir-SpiroPNP having the structure of formula II according to claim 6, wherein, the chiral spirocyclic phosphine-nitrogen-phosphine tridentate iridium catalyst Ir-SpiroPNP having the structure of formula II is in solvated or non-solvated state.

9. A method for synthesizing the chiral spirocyclic phosphine-nitrogen-phosphine tridentate iridium catalyst Ir-SpiroPNP having structure of formula II according to claim 6, comprising the following steps:

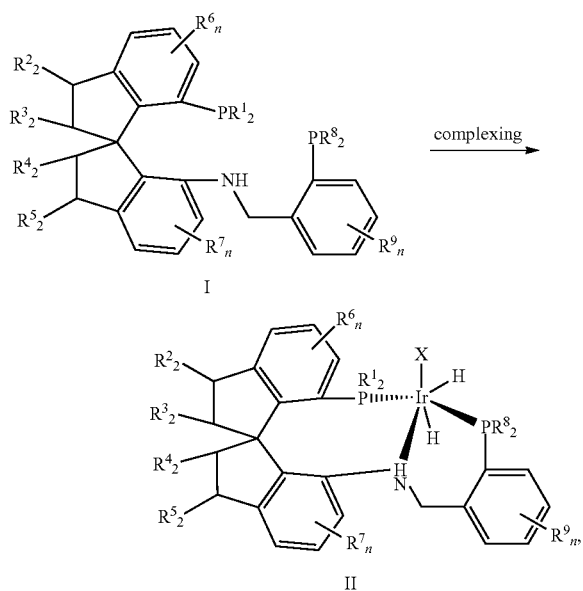

I

II

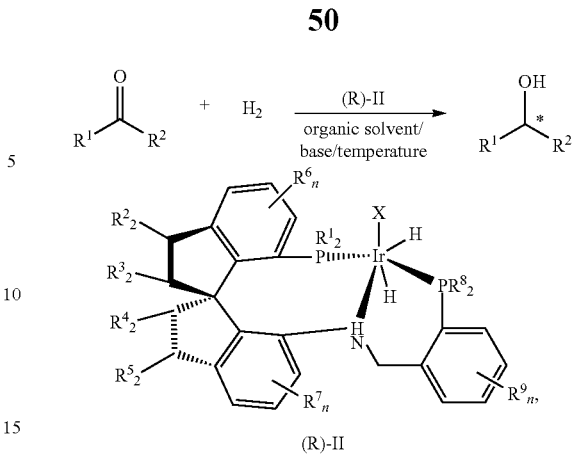

(R)-II adding the chiral spirocyclic phosphine-nitrogen-phosphine tridentate ligand having structure formula I and an iridium salt precursor into an organic solvent, heating at the temperature between 70° C.-100° C. and under 0.1-20 atm hydrogen atmosphere, stirring and reacting for 10-24 hours to obtain the chiral spirocyclic phosphine-nitrogen-phosphine tridentate iridium catalyst Ir-SpiroPNP having the structure of formula II, wherein, $R^1$ to $R^9$ in formula I, II are defined as in claim 1, X is $Cl^-$, $Br^-$, $OMe^-$, $BF_4^-$ or $OTf^-$, a molar ratio of the chiral spirocyclic phosphine-nitrogen-phosphine tridentate ligand having the structure of formula I and the iridium salt precursor is 1:1 to 2:1, the iridium salt precursor is selected from $[Ir(COD)Cl]_2$, $[Ir(COD)_2]BF_4$, $[Ir(COD)_2]PF_6$, $[Ir(COD)_2]S_bF_6$, and $[Ir(COD)_2]OTf$, wherein COD equals to cyclooctadiene, and Tf equals to $SO_2CF_3$.

10. A method of using the chiral spirocyclic phosphine-nitrogen-phosphine tridentate iridium catalyst Ir-SpiroPNP having the structure of formula II thereof according to claim 6, comprising the following reaction steps:

adding a compound having a carbonyl functional group to an organic solvent, a base in the presence of the chiral spirocyclic phosphine-nitrogen-phosphine tridentate iridium catalyst Ir-SpiroPNP having the formula II, under 1-100 atmosphere of hydrogen, by an asymmetric catalytic hydrogenation reaction to obtain an alcohol compound.

11. The method of using the chiral spirocyclic phosphine-nitrogen-phosphine tridentate iridium catalyst Ir-SpiroPNP having the structure of formula II according to claim 10 comprising the reaction steps of adding a compound having a carbonyl functional group, in the presence of a base and an organic solvent, in the presence of iridium catalyst Ir-SpiroPNP, at the hydrogen atmosphere condition with value range of 1-100 atm, and reacting for 0.1-80 hours to obtain chiral alcohol compounds.

12. The method of using the chiral spirocyclic phosphine-nitrogen-phosphine tridentate iridium catalyst Ir-SpiroPNP having the structure of formula II according to claim 10, wherein, the molar ratio of the compound having a carbonyl functional group to the catalyst is 100:1 to 500,000:1 the concentration of the compound having a carbonyl functional group is 0.001 to 10.0 M;

wherein the base is selected from the group consisting of sodium hydroxide, potassium hydroxide, sodium carbonate, potassium carbonate, sodium ethoxide, potassium ethoxide, sodium tert-butoxide, potassium tert-butoxide, lithium tert-butoxide, triethylamine, tributylamine and N-methylmorpholine, the concentration of the base is 0.005 M to 1.0 M; the reaction temperature is 0° C. to 80° C.

* * * * *